(12) United States Patent
Davis et al.

(10) Patent No.: US 9,457,052 B2
(45) Date of Patent: Oct. 4, 2016

(54) ALLOGRAFT TOLERANCE INDUCTION

(71) Applicants: Thomas A. Davis, Oak Hill, VA (US); Khairul Anam, Gaithersburg, MD (US); Eric A. Elster, Kensington, MD (US); Douglas K. Tadaki, Frederick, MD (US)

(72) Inventors: Thomas A. Davis, Oak Hill, VA (US); Khairul Anam, Gaithersburg, MD (US); Eric A. Elster, Kensington, MD (US); Douglas K. Tadaki, Frederick, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/210,701

(22) Filed: Mar. 14, 2014

(65) Prior Publication Data

US 2015/0258144 A1  Sep. 17, 2015
US 2016/0256489 A9  Sep. 8, 2016

Related U.S. Application Data

(60) Provisional application No. 61/788,407, filed on Mar. 15, 2013.

(51) Int. Cl.
| | | |
|---|---|---|
| *A61K 35/28* | (2015.01) | |
| *A61K 45/06* | (2006.01) | |
| *A61K 31/255* | (2006.01) | |
| *A61K 39/00* | (2006.01) | |
| *C12N 5/073* | (2010.01) | |
| *C12N 5/0775* | (2010.01) | |
| *A61K 35/12* | (2015.01) | |

(52) U.S. Cl.
CPC ............ *A61K 35/28* (2013.01); *A61K 31/255* (2013.01); *A61K 39/001* (2013.01); *A61K 45/06* (2013.01); *C12N 5/0605* (2013.01); *C12N 5/0667* (2013.01); *C12N 5/0668* (2013.01); *A61K 2035/122* (2013.01)

(58) Field of Classification Search
CPC ............................ A61K 35/12; A61K 35/545
See application file for complete search history.

(56) References Cited

U.S. PATENT DOCUMENTS

2010/0150947 A1* 6/2010 Siemionow ................ 424/173.1
2011/0064709 A1* 3/2011 Miller et al. ................ 424/93.71

OTHER PUBLICATIONS

Anam K. et al. Amnion Derived Multipotent Progenitor Cells Support Allograft Tolerance Induction. Am J Transplantation 13(6)1416-1428, Jun. 2013.*
Li J. et al. Prolongation of Cardiac Allograft Survival by Syngeneic Hematopoietic Stem/Progenitor Cell Transplantation in Mice. Advances in Therapy 25(9)935-942, Sep. 2008.*
Rachamim N. et al. Tolerance Induction by Megadose Hematopoietic Transplants. Transplantation 65(10)1386-1393, May 27, 1998.*
Anam K. et al. Infusion of Lin—Bone Marrow Cells Results in Multilineage Macrochimerism . . . Transplant Immunology 24:69-75, 2010.*
Fu, F. et al. Costimulatory Molecule Deficient Dendritic Cell Progenitors Prolong Cardiac Allograft Survival . . . Transplantation 62(5)659-665, Sep. 1996.*
Webber A, Hirose R, Vincenti F, Novel strategies in immunosuppression: issues in perspective. Transplantation. 2011;91(10):1057-64. Epub Mar. 18, 2011.
Girlanda R, Kirk AD. Frontiers in nephrology: immune tolerance to allografts in humans. Journal of the American Society of Nephrology : JASN. 2007;18(8):2242-51. Epub Jul. 20, 2007.
Kirk AD. Clinical tolerance 2008. Transplantation. 2009;87(7):953-5. Epub Apr. 9, 2009.
Parolini O, Soncini M, Evangelista M, Schmidt D. Amniotic membrane and amniotic fluid-derived cells: potential tools for regenerative medicine? Regenerative medicine. 2009;4(2):275-91. Epub Mar. 26, 2009.
Soncini M, Vertua E, Gibelli L, Zorzi F, Denegri M, Albertini A, et al. Isolation and characterization of mesenchymal cells from human fetal membranes. Journal of tissue engineering and regenerative medicine. 2007;1 (4):296-305. Epub Nov. 27, 2007.
Manuelpillai U, Moodley Y, Borlongan CV, Parolini O. Amniotic membrane and amniotic cells: potential therapeutic tools to combat tissue inflammation and fibrosis? Placenta. 2011;32 Suppl 4:S320-5. Epub May 17, 2011.
Cargnoni A, Di Marcello M, Campagnol M, Nassuato C, Albertini A, Parolini O. Amniotic membrane patching promotes ischemic rat heart repair. Cell transplantation. 2009;18(10):1147-59. Epub Aug. 5, 2009.
Cargnoni A, Ressel L, Rossi D, Poli A, Arienti D, Lombardi G, et al. Conditioned medium from amniotic mesenchymal tissue cells reduces progression of bleomycin-induced lung fibrosis. Cytotherapy. 2012;14(2):153-61. Epub Oct. 1, 2011.
Cargnoni A, Gibelli L, Tosini A, Signoroni PB, Nassuato C, Arienti D, et al. Transplantation of allogeneic and xenogeneic placenta-derived cells reduces bleomycin-induced lung fibrosis. Cell transplantation. 2009;18 (4):405-22. Epub Jul. 23, 2009.
Chen Z, Tortella FC, Dave JR, Marshall VS, Clarke DL, Sing G, et al. Human amnion-derived multipotent progenitor cell treatment alleviates traumatic brain injury-induced axonal degeneration. Journal of neurotrauma. 2009;26(11)1987-97. Epub Nov. 6, 2009.
Tsuji H, Miyoshi S, Ikegami Y, Hida N, Asada H, Togashi I, et al. Xenografted human amniotic membrane-derived mesenchymal stem cells are immunologically tolerated and transdifferentiated into cardiomyocytes. Circulation research. 2010;106(10):1613-23. Epub May 29, 2010.
Zhang D, Jiang M, Miao D. Transplanted human amniotic membrane-derived mesenchymal stem cells ameliorate carbon tetrachloride-induced liver cirrhosis in mouse. PloS one. 2011;6(2):e16789. Epub Feb. 18, 2011.

(Continued)

*Primary Examiner* — Ralph Gitomer
(74) *Attorney, Agent, or Firm* — Albert M. Churilla; Ning Yang; Diane P. Tso

(57) ABSTRACT

A method inducing chimerism and allograft tolerance by co-infusion of stem/progenitor-like cells and donor cells, wherein the donor cells can be bone marrow cells. The method also comprises the conditioning comprising depletion of CD4+ and CD8+ T-cells and administration of low doses of anti-neoplastic drugs. The inventive method comprises an aspect wherein allograft tolerance is induced without systemically suppressing the immune system.

10 Claims, 14 Drawing Sheets

(56) References Cited

OTHER PUBLICATIONS

Banas RA, Trumpower C, Bentlejewski C, Marshall V, Sing G, Zeevi A. Immunogenicity and immunomodulatory effects of amnion-derived multipotent progenitor cells. Human immunology. 2008;69(6):321-8. Epub Jun. 24, 2008.
Wolbank S, Peterbauer A, Fahrner M, Hennerbichler S, Van Griensven M, Stadler G, et al. Dose-dependent immunomodulatory effect of human stem cells from amniotic membrane: a comparison with human mesenchymal stem cells from adipose tissue. Tissue engineering. 2007;13(6):1173-83. Epub May 24, 2007.
Magatti M, De Munari S, Vertua E, Gibelli L, Wengler GS, Parolini O. Human amnion mesenchyme harbors cells with allogeneic T-cell suppression and stimulation capabilities. Stem cells. 2008;26(1):182-92. Epub Sep. 29, 2007.
Magatti M, De Munari S, Vertua E, Nassauto C, Albertini A, Wengler GS, et al. Amniotic mesenchymal tissue cells inhibit dendritic cell differentiation of peripheral blood and amnion resident monocytes. Cell transplantation. 2009;18(8):899-914. Epub Jun. 16, 2009.
Liu YH, Vaghjiani V, Tee JY, To K, Cui P, Oh DY, et al. Amniotic epithelial cells from the human placenta potently suppress a mouse model of multiple sclerosis. PloS one. 2012;7(4):e35758. Epub May 9, 2012.
Steed DL, Trumpower C, Duffy D, Smith C, Marshall V, Rupp R, et al. Amnion-derived cellular cytokine solution: a physiological combination of cytokines for wound healing. Eplasty. 2008;8:e18. Epub May 8, 2008.
Anam K, Akpinar E, Craighead N, Black AT, Hale DA. Targeted T-cell depletion or CD154 blockade generates mixed hemopoietic chimerism and donor-specific tolerance in mice treated with sirolimus and donor bone marrow. Transplantation. 2004;78(9)1290-8. Epub Nov. 19, 2004.
Pilat N, Baranyi U, Klaus C, Jaeckel E, Mpofu N, Wrba F, et al. Treg-therapy allows mixed chimerism and transplantation tolerance without cytoreductive conditioning. American journal of transplantation : official journal of the American Society of Transplantation and the American Society of Transplant Surgeons. 2010;10(4):751-62. Epub Feb. 13, 2010.
Domenig C, Sanchez-Fueyo A, Kurtz J, Alexopoulos SP, Mariat C, Sykes M, et al. Roles of deletion and regulation in creating mixed chimerism and allograft tolerance using a nonlymphoablative irradiation-free protocol. Journal of immunology. 2005;175(1):51-60. Epub Jun. 24, 2005.
Xu H, Chilton PM, Huang Y, Schanie CL, Ildstad ST. Production of donor T cells is critical for induction of donor-specific tolerance and maintenance of chimerism. Journal of immunology. 2004;172(3):1463-71. Epub Jan. 22, 2004.
Akpinar E, Craighead N, Smkoot D, Hale DA. Potent skin allograft survival prolongation using a committed progenitor fraction of bone marrow in mice. Transplantation. 2004;78(3):383-91. Epub Aug. 19, 2004.
Velasquez-Lopera MM, Eaton VL, Lerret NM, Correa LA, Decresce RP, Garcia LF, et al. Induction of transplantation tolerance by allogeneic donor-derived CD4(+)CD25(+)Foxp3(+) regulatory T cells. Transplant immunology. 2008;19(2):127-35. Epub May 28, 2008.
Hodges RJ, Lim R, Jenkin G, Wallace EM. Amnion epithelial cells as a candidate therapy for acute and chronic lung injury. Stem cells international. 2012;2012:709763. Epub May 12, 2012.
Murphy S, Lim R, Dickinson H, Acharya R, Rosli S, Jenkin G, et al. Human amnion epithelial cells prevent bleomycin-induced lung injury and preserve lung function. Cell transplantation. 2011;20(6):909-23. Epub Nov. 26, 2010.
Danchuk S, Ylostalo JH, Hossain F, Sorge R, Ramsey A, Bonvillain RW, et al. Human multipotent stromal cells attenuate lipopolysaccharide-induced acute lung injury in mice via secretion of tumor necrosis factor-alpha-induced protein 6. Stem cell research & therapy. 2011;2(3):27. Epub May 17, 2011.
Carosella ED, Moreau P, Le Maoult J, Le Discorde M, Dausset J, Rouas-Freiss N. HLA-G molecules: from maternal-fetal tolerance to tissue acceptance. Advances in immunology. 2003;81:199-252. Epub Jan. 9, 2004.
Giuliani M, Fleury M, Vernochet A, Ketroussi F, Clay D, Azzarone B, et al. Long-lasting inhibitory effects of fetal liver mesenchymal stem cells on T-lymphocyte proliferation. PloS one. 2011;6(5):e19988. Epub Jun. 1, 2011.
Roelen DL, Van Der Mast BJ, in't Anker PS, Kleijburg C, Eikmans M, van Beelen E, et al. Differential immunomodulatory effects of fetal versus maternal multipotent stromal cells. Human immunology. 2009;70(1):16-23. Epub Nov. 18, 2008.
Liang S, Horuzsko A. Mobilizing dendritic cells for tolerance by engagement of immune inhibitory receptors for HLA-G. Human immunology. 2003;64(11):1025-32. Epub Nov. 7, 2003.
Liang S, Ristich V, Arase H, Dausset J, Carosella ED, Horuzsko A. Modulation of dendritic cell differentiation by HLA-G and ILT4 requires the IL-6—STAT3 signaling pathway. Proceedings of the National Academy of Sciences of the United States of America. 2008;105(24):8357-62. Epub Jun. 14, 2008.
Selmani Z, Naji A, Zidi I, Favier B, Gaiffe E, Obert L, et al. Human leukocyte antigen-G5 secretion by human mesenchymal stem cells is required to suppress T lymphocyte and natural killer function and to induce CD4 +CD25highFOXP3+ regulatory T cells. Stem cells. 2008;26(1):212-22. Epub Oct. 13, 2007.
Le Rond S, Azema C, Krawice-Radanne I, Durrbach A, Guettier C, Carosella ED, et al. Evidence to support the role of HLA-G5 in allograft acceptance through induction of immunosuppressive/regulatory T cells. Journal of immunology. 2006;176(5):3266-76. Epub Feb. 24, 2006.
Francois M, Romieu-Mourez R, Li M, Galipeau J. Human MSC suppression correlates with cytokine induction of indoleamine 2,3-dioxygenase and bystander M2 macrophage differentiation. Molecular therapy : the journal of the American Society of Gene Therapy. 2012;20(1)187-95. Epub Sep. 22, 2011.
Ren G, Su J, Zhang L, Zhao X, Ling W, L'Huillie A, et al. Species variation in the mechanisms of mesenchymal stem cell-mediated immunosuppression. Stem cells. 2009;27(8):1954-62. Epub Jun. 23, 2009.
Hass R, Kasper C, Bohm S, Jacobs R. Different populations and sources of human mesenchymal stem cells (MSC): A comparison of adult and neonatal tissue-derived MSC. Cell communication and signaling : CCS. 2011;9:12. Epub May 17, 2011.
Sheng H, Wang Y, Jin Y, Zhang Q, Zhang Y, Wang L, et al. A critical role of IFNgamma in priming MSC-mediated suppression of T cell proliferation through up-regulation of B7-H1. Cell research. 2008;18(8):846-57. Epub Jul. 9, 2008.
Kronsteiner B, Wolbank S, Peterbauer A, Hackl C, Redl H, Van Griensven M, et al. Human mesenchymal stem cells from adipose tissue and amnion influence T-cells depending on stimulation method and presence of other immune cells. Stem cells and development. 2011;20(12):2115-26. Epub Mar. 9, 2011.
Ryan JM, Barry F, Murphy JM, Mahon BP. Interferon-gamma does not break, but promotes the immunosuppressive capacity of adult human mesenchymal stem cells. Clinical and experimental immunology. 2007;149(2):353-63. Epub May 25, 2007.
Meisel R, Zibert A, Laryea M, Gobel U, Daubener W, Dilloo D. Human bone marrow stromal cells inhibit allogeneic T-cell responses by indoleamine 2,3-dioxygenase-mediated tryptophan degradation. Blood. 2004;103 (12):4619-21. Epub Mar. 6, 2004.
Gimble JM, Bunnell BA, Frazier T, Rowan B, Shah F, et al. (2013) Adipose-derived stromal/stem cells: a primer. Organogenesis 9: 3-10.
McIntosh KR, Frazier T, Rowan BG, Gimble JM (2013) Evolution and future prospects of adipose-derived immunomodulatory cell therapeutics. Expert Rev Clin Immunol 9: 175-184.

\* cited by examiner

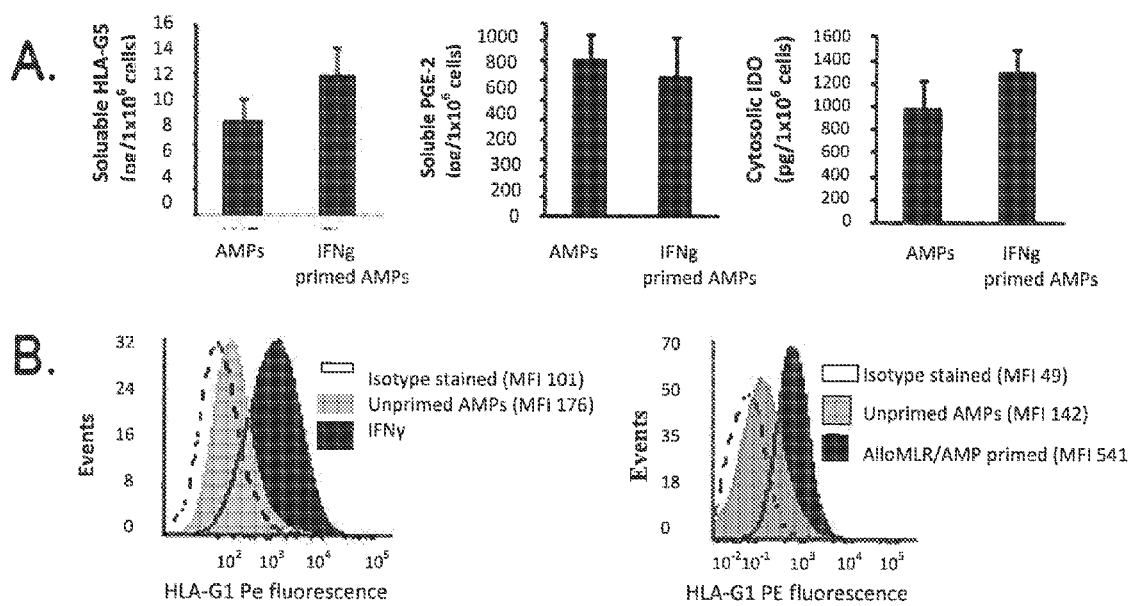
FIG. 3A/B

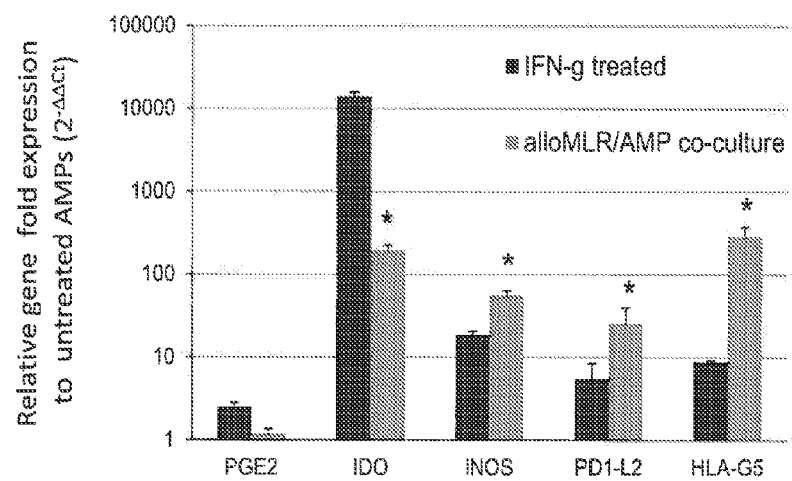
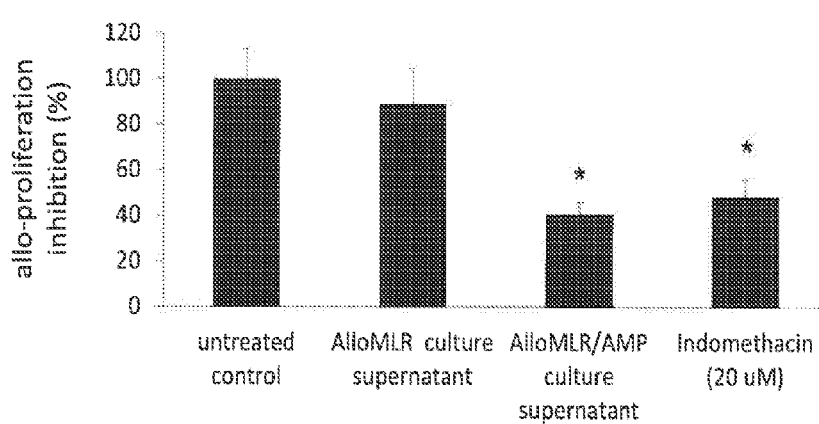
FIG. 3C/D

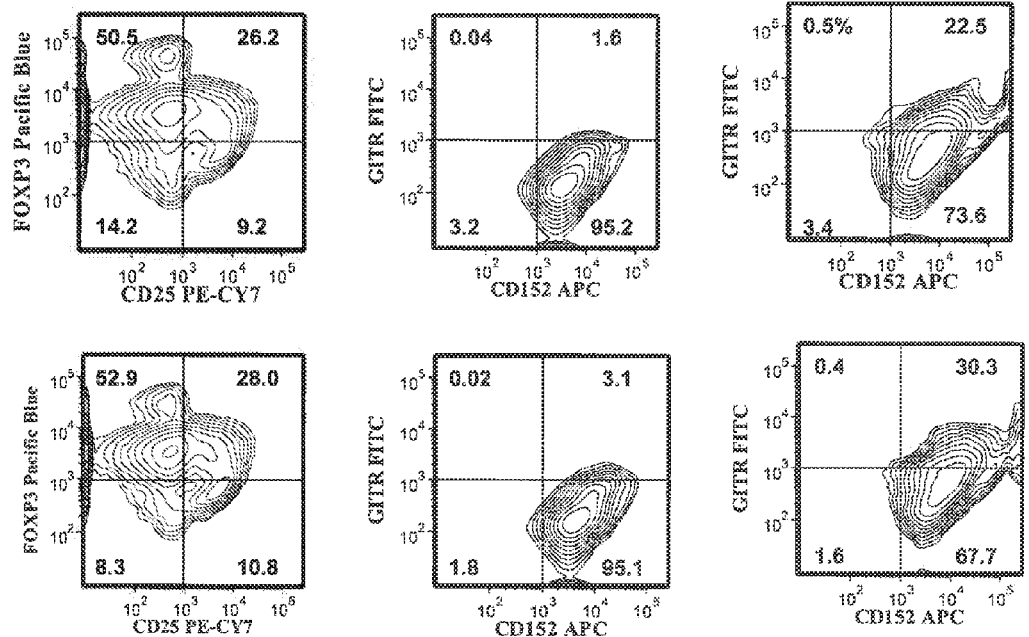
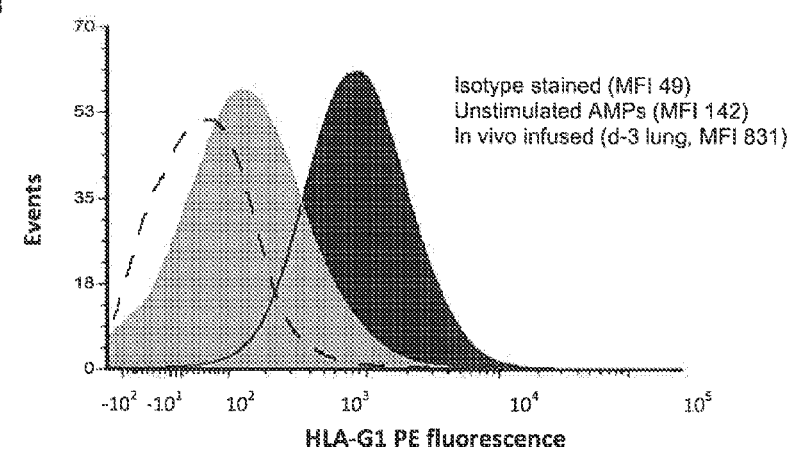
FIG. 10

ALLOGRAFT TOLERANCE INDUCTION

CROSS-REFERENCE TO RELATED APPLICATIONS

This application claims the benefit of provisional application No. 61/788,407, filed Mar. 15, 2013.

BACKGROUND OF INVENTION

1. Field of Invention

The inventive subject matter relates to a method of inducing immune allograft tolerance and chimerism.

2. Background Art

Activated T-cells orchestrate the rejection of vascularized allografts unless multiple components of an alloimmune response are indefinitely attenuated. These in vivo corrections are typically achieved through the long-term administration of potent immunosuppressive drugs that nonspecifically block T-cell activation, proliferation and function while trying to avoid the deleterious consequences of over immunosuppression (1, 2). In contrast, therapies to induce tolerance, which exploit the immune system's endogenous regulatory mechanisms through clonal deletion of alloreactive T-cells and the induction of donor CD4+ regulatory cell populations ($T_{regs}$) (3-5), have been more difficult to achieve. In various experimental animal models, T-cell depletion, T-cell costimulation blockade, and/or donor hematopoietic cell infusion/chimerism have been shown to promote organ specific immune tolerance after transplantation (1, 4, 6). However, clinical success has been limited and unpredictable (5, 7).

Recently, the immunoregulatory properties of a number of tissue mesenchymal stromal cells (MSC) or MSC-like populations, mainly bone marrow and adipose tissue-derived cells, have attracted a lot of attention as potential therapeutic cell sources for use in tolerance induction cell therapies. Human amnion epithelial cells (hAECs) derived from the embryonic epiblast, are immunologically tolerated cells suppress T-cell allogeneic proliferation responses in mixed lymphocyte reaction (MLR) cultures wherein hypo-responsiveness is mediated via cell-to-cell contact with target immune cells and secretion of soluble mediators (PGE-2 and TGFβ1) plus the inhibition of the differentiation and maturation of monocytes into dendritic cells (DCs) resulting in an impaired allostimulation function on T-cells (8-21). Here we show that the administration of AMPs combined with a clinically feasible regimen of CD4+/CD8+ cell depletion, low dose busulfan conditioning and limited numbers of unfractionated donor bone marrow cells result in stable multilineage donor cell chimerism induction, indefinite allograft acceptance, and donor cell specific tolerance in the absence of long-term immunosuppressive treatment.

SUMMARY OF THE INVENTION

The current invention relates to a method of inducing chimerism and allograft tolerance in graft verses host responses by administration of stem/progenitor-like cells and donor cells.

In a preferred embodiment, donor, unfractionated bone marrow cells (BMCs) are co-infused with stem/progenitor-like cells, although other sources of donor cells are envisioned. In another embodiment, CD4+ and CD8+ cells are depleted prior to infusion of stem/progenitor-like cells and BMCs. Depletion of CD4+ and CD8+ can be accompanied with other chemotherapeutic drugs, including anti-neoplastic agents or other chemotherapeutic drugs, including those used in transplantation procedures, including bone marrow transplantation. As an example, depletion of CD4+ and CD8+ can be accompanied by administration of busulfan.

Stem/progenitor-like cells can be derived from a number of different functional cell types or cellular lineages. In a preferred embodiment, the stem/progenitor-like cells are derived from adipose cells.

BRIEF DESCRIPTION OF DRAWINGS

FIG. 3. Effect of IFNγ on production of immunoregulatory molecules by AMPs. (A) Secretion of soluble HLA-G (HLA-G5, n=13 separate experiments), PGE-2 (n=8 separate experiments) and cytosolic IDO (n=2 separate experiments) by untreated and IFNγ-treated AMPs for 48 h measured by ELISA. Results are expressed as the mean value±SD. (B) Representative flow cytometry histograms showing mHLA-G1 expression (median fluorescent intensity, MFI) on untreated and IFNγ-treated AMPs after 48 h of culture (n=5 different cultures) (C) Expression pattern of PGE-2, IDO, PD1L2 and iNOS immunoregulatory molecules in IFNγ-treated AMP and allo-MLR/AMP cultures after 48 h of culture by RT-PCR analysis. Bars indicate mean fold increase±SD mRNA expression level of the indicated gene relative the housekeeping gene GAPDH and normalized to untreated AMP cutlures. (D) Supernatants from allo-MLR/AMP co-cultures inhibit MLR lymphocyte proliferation. Naive C57BL/6 splenocytes (as responders cells) were cultured 1:1 with irradiated (3 Gy) naïve BALB/c stimulatory cells. Supernatants (10% final plating dilution) from day 5 allo-MLR cultures, allo-MLR/AMP co-cultures or indomethacin (20 µM) was added to the MLR at the onset of culture. Cell proliferation was analyzed by $^3$H-thymidine incorporation during the last 18 h of a 5 day culture. Results are expressed as the mean percent alloproliferation inhibition of quadruplicate cultures.

FIG. 10. (A) Representative flow cytometry histograms showing mHLA-G1 expression (median fluorescent intensity, MFI) on untreated AMPs and AMP entrapped in the lung of skin transplanted mice at day 3 post BMC+AMP co-infusion (day 10 post skin grafting; n=10 mice). (B) Representative flow cytometric analysis of splenic $T_{regs}$ at day 10 post skin grafting and day 3 post BMC and BMC+AMP infusion. Contour plots show gated CD45$^+$CD4$^+$ T-cells stained with anti-CD25, anti-CD152, anti-GITR and then intracellularly with anti-Foxp3. Left panels are gated on CD45$^+$CD4$^+$ cells, middle panels gated on CD45$^+$CD25$^-$Foxp3$^+$ cells and right panels gated on CD45$^+$CD25$^+$Foxp3$^+$ cells. The number indicates the percentage of cells in the corresponding quadrant. Quadrants are set according to isotype controls. Results shown are representative of five mice per group.

DETAILED DESCRIPTION OF PREFERRED EMBODIMENTS

As used herein, stem/progenitor-like cells refer to cells that are capable of giving rise to specialized cells with specific functional properties. Stem/progenitor-like cells can be derived from a number of sources. The important property is that they be capable of differentiating into multiple cell types and functions. Examples include, but are not limited to: mesenchymal stem cells, adipose-derived stem cells, cord blood stem cells, placental stem cells, bone marrow cells, circulating peripheral blood stem cells, and cytokine mobilized stem cells. The term Donor cells refers to cells capable of developing an immunologically functional chimera. These include unfractionated bone marrow cells (BMC) but can also include: stem cells, committed progenitor cells, differentiated cells, bone marrow cells, cells derived from cord blood or mobilized stem cell. Bone marrow cells, for example, can be derived from cord blood, vertebral body bone marrow cells, marrow cells isolated from ribs, iliac crest, long bones, umbilical cord blood, or mobilized stem cells.

Attenuation of alloimmune responses against vascularized allografts is important in transplantation medical procedures. However, for long-term survival of allografts, immunosuppressive drugs are typically employed.

The current inventive method provides a means for survival of allografts or tissue transplants, through the induction of macrochimerism and transplantation tolerance through the administration of human stem/progenitor-like cells and donor cells. A number of stem/progenitor-like cells can be used. Examples of acceptable cells include, but are not limited to: mesenchymal stem cells, adipose-derived stem cells, cord blood stem cells, placental stem cells, bone marrow cells, circulating peripheral blood stem cells, and cytokine mobilized stem cells. Therefore, embodiments of the invention include the use of human stem/progenitor-like cells derived from different sources.

Figure 1:
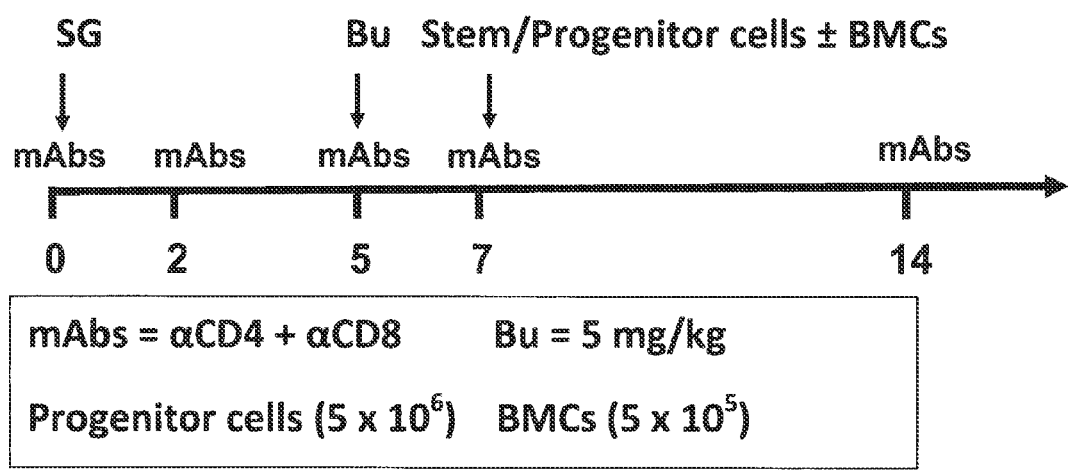
FIG. 1. Experimental protocol for inducing skin allograft tolerance. C57BL/6 mice (H-2$^b$) were treated with a skin allograft (skin graft: BALB/c; H-2$^d$) on day 0. Injections of anti-mouse CD4 and anti-CD8 (mAbs) were given i.p. on days 0, +2, +5, +7, and +14. Mice were treated with a single dose of busulfan (Bu) i.p. on day +5. At day 7 post skin transplantation, progenitor cells (5×10$^6$) and/or BMCs (5×10$^5$) were infused intravenously though the lateral tail vein.

Regardless of the source of the human stem/progenitor-like cells, the inventive method comprises induction of tolerance through the administration of the human stem/progenitor-like cells generally according to the method depicted in FIG. 1, although variations in the general scheme are envisioned including the human stem/progenitor-like cells type used, donor cells used, and when the cells are administered relative to the transplantation of the tissue. The method can also comprise depletion of CD4$^+$ and CD8$^+$ cells. In another embodiment, the inventive method comprises the administration of chemotherapeutic agents. An example, for illustration, the chemotherapeutic agent busulfan is administered.

Allo-MLR Assay

In accessing tolerance induction, mixed lymphocyte responses (MLR) assays were performed. In the assays, 5×10$^5$ responding C57BL/6 splenocytes with 5×10$^5$ BALB/c irradiated (30 Gy $^{137}$Cs) splenocytes. Cells were cultured U-bottom 96-well plates in complete culture medium consisting of RPMI 1640 supplemented with 10% FBS, 10 mM HEPES, 1% nonessential amino acids, 2 mM L-glutamine, 100 U/ml penicillin, 100 µg/ml streptomycin (all from Invitrogen), and 5 µg/mL 2-mercaptoethanol (Sigma-Aldrich) at 37° in a humidified atmosphere of 5% CO$_2$/95% air for 5 days. Irradiated AMPs were added at 5×10$^5$/well for standard assays or in graded numbers in titration experiments in the presence or absence of 20 µM indomethacin (Sigma Aldrich, St. Louis, Mo.). Wells were pulsed with 1.0 mCi [$^3$H]-thymidine for the last 18 h of culture. $^3$H-thymidine incorporation was measured using a scintillation counter (Microbeta$^+$, LKB-Wallac, Turku, Finland). Results expressed as percent control allo reactivity (test c.p.m./control allo-MLR c.p.m.×100). mHLA-G on AMPs in allo-MLR cultures was detected via flow cytometry analysis and sHLA-G production by ELISA (Biovendor, Chandler, N.C., USA). The percentage of CD4$^+$CD25$^+$ T cells and CD4$^+$CD25$^+$Foxp3$^+$ T cells was measured by FACS.

Skin Grafting

In the studies, full thickness trunk skin grafts (4 cm$^2$) from BALB/c and C3H/HEJ mice were transplanted onto the dorsal flanks of C57BL/6 recipient mice and secured with an adhesive bandage for 7 days (23).

Immuno-Conditioning and Allogeneic Bone Marrow+Xenogeneic Infusion Protocol

As illustrated in FIG. 1, five doses of a cocktail of CD4-α (YTS 191.1, 10 mg/Kg) and CD8-α mAbs (YTS 169.4, 10 mg/Kg) were administered (i.p) on day 0, +2, +5, +7, and +14 relative to skin grafting on day 0 (23, 24). A single nonmyeloablative low dose of busulfan (5 mg/kg, i.p; Sigma-Aldrich) was given on day +5 (23). It is anticipated that the dose of busulfan be low (5 to 1 mg/kg) or less. At day +7 post skin transplantation, donor bone marrow cells (5×10$^5$) were infused i.v. with or without AMPs (5×10$^6$ cells i.v. in D-PBS containing 100 U/ml preservative free heparin (Sigma-Aldrich) and 100 U/ml DNase containing 5 mM Mg$^{2+}$ (Worthington, Lakewood, N.J.). In addition, the impact of these treatments alone and in various combinations on the extent of chimerism and allograft survival was assessed. We found the addition of heparin and DNase in the infusion medium minimizes cellular aggregation and lethal pulmonary embolic events at the time of progenitor cell infusion.

Analysis of Multilineage Chimerism and Clonal Cell Deletion

Fluorochrome labeled antibodies to the following markers were used to determine chimerism and to enumerate T$_{regs}$; H2D$^d$, CD3, CD4, CD8, CD11b, CD11c, CD19, CD25, CD45, CD31, CD49b, CD152, PAN-NK, NKT, Foxp3, Vβ11, Vβ5.1/2, Vβ8.1/2, –γδ TCR, GITR and MHC II. Irrelevant isotype-matched antibodies were used as negative controls. Polychromatic flow cytometric analysis was performed using a BD FACS Aria II flow cytometer (Becton Dickinson, San Jose, Calif.).

Suppressor-Regulatory Cell Allo-MLR Assay

Irradiated splenocytes from tolerant recipients (putative regulatory cells) were added to allo-MLR cultures in graded numbers in titration experiments with a fixed number of responder cells (5×10$^5$). BrdU incorporation was detected by ELISA (Roche, San Francisco, Calif., USA). The results are expressed as net absorbance of stimulated cells minus absorbance of unstimulated cells.

Example 1

AMP Inhibition of Allograft Dependent Proliferation in Murine T-Cells

Amnion-Derived Multipotent Progenitor Cells (AMPs)

AMPs were obtained from Stemnion, Inc (Pittsburgh, Pa., USA). The cells were stored in liquid nitrogen until infusion (17, 22). For some experiments AMPs were thawed, and immediately fluorescently pre-labeled prior to infusion using CFSE (Molecular Probes/Invitrogen, Gaithersburg, Md., USA).

AMP Cell Trafficking

Skin transplanted mice were co-infused with BMC+CFSE-labeled AMPs on day-7 post grafting. Mice were killed at 0 and 4 h and at days 1, 2, 3, 6, 7, 12 and 14 post infusion. Lungs, liver (~⅓), spleen, lymph nodes (pooled brachial, axillary and inguinal), thymus, bone marrow, kidney, mesenteric intestine, and parietal peritoneum were harvested and stored in RNALATER™ (QIAGEN Science, Germantown, Md.). RNA was isolated with TRIZOL® reagent (Life Technologies, Carlsbad, Calif.) and extracted from the tissues using the QIAGEN RNEASY® LIPID Kit (QIAGEN). Reverse transcriptase polymerase chain reaction (RT PCR) was used to convert 1 μg of RNA to cDNA. qRT-PCR for human β-actin was used to detect xenogeneic human AMPs. Mouse β-actin was used as the housekeeping gene for normalization during qRT-PCR. In some experiments, lungs were frozen in OCT, sectioned (5 μm thick), and examined for CFSE positive cells.

Cytokine, sHLA-G and Immunomodulatory Gene Expression Measurements

Cells and culture supernatants were collected from 48 h allo-MLR cultures and AMP cultures ($1 \times 10^6$ AMPs/ml) treated ±IFN-γ (10 ng/ml). Culture supernatants were collected and stored at −80° C. until analysis using a Th1/Th2 cytokine 6-plex LUMINEX® assay (Invitrogen, Carlsbad, Calif.), $PGE_2$ ELISA (Cayman Chemical Company, Ann Arbor, Mich. USA) and sHLA-G ELISA. Cytosolic IDO protein was analyzed from cell lysates (Novatein Biosciences, Cambridge, Mass. USA). Total mRNA was prepared as indicated above. The $2^{-\Delta\Delta Ct}$ method was used to calculate relative fold changes in gene expression using qRT-PCR.

Statistics

Time to skin graft rejection was represented by Kaplan-Meier survival curves, and comparison of graft survival was calculated using log-rank assessment. Additional statistical analysis was performed using a two-tailed unpaired Student t test. A p value of <0.05 was considered significant for all tests (GRAPHPAD™ Software, San Diego, Calif., USA).

Figure 2:
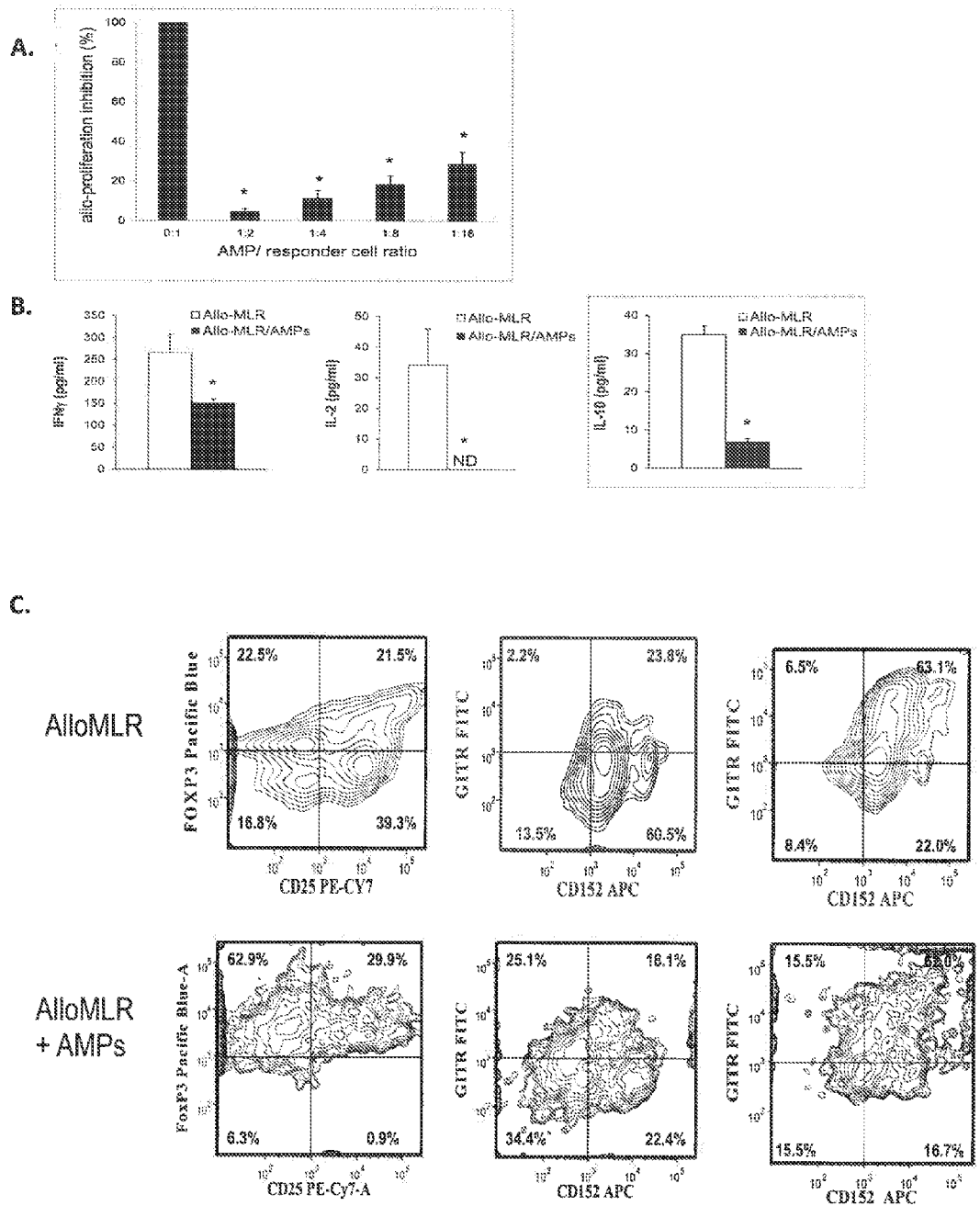
FIG. 2. AMPs inhibit allo-MLR lymphocyte proliferation. (A) Naive C57BL/6 splenocytes (as responders cells) were cultured 1:1 with irradiated (3 Gy) naïve BALB/c stimulatory cells. AMPs were added to the MLR at the onset of culture at the indicated responder to AMP cell ratios. Cell proliferation was analyzed by 3H-thymidine incorporation during the last 18 h of a 5 day culture. Results are expressed as the mean percent alloproliferation inhibition of quadruplicate cultures. Data are representative of two independent experiments. (B) Cytokine analysis of 48 h culture supernatants obtained from mixed lymphocyte reaction assays. Data are presented as means±SD (n=3; P<0.05). (C) Representative flow cytometric analysis of splenic $T_{regs}$ following 5 days of alto-MLR culture in the absence and presence of AMP co-culture. Contour plots show gated CD45+CD4+ T-cells stained with anti-CD25, anti-CD152, anti-GITR and then intracellularly with anti-Foxp3. Left panels are gated on CD45+ CD4+ cells, middle panels gated on CD45+CD25− Foxp3+ cells and right panels gated on CD45+CD25+Foxp3+ cells. The number indicates the percentage of cells in the corresponding quadrant. Quadrants are set according to isotype controls. Results shown are representative of three separate experiments.

In the study, allo-MLR proliferation was inhibited >95% in the presence of AMPs at a cell ratio of 1 AMP per 4 responder splenocytes (1:4); significant suppression was also observed at a ratio of 1:16 (FIG. 2A). A comparison of Th1/Th2 cytokines during 48 h allo-MLR culture showed that IL-2 was below detection limits (<5 pg/ml) and IFNγ and IL-10 production was significantly less in co-cultures with AMPs (FIG. 2B; P<0.05), whereas IL-4, IL-5 and IL-12 were extremely low in both culture conditions (data not shown). After 5 days of culture the proportion of responder $CD4^+CD25^+Foxp3^+CD152^+GITR^+$ $T_{regs}$ was higher following AMP co-culture (FIG. 2C; 18.5% versus 13.6%). Interestingly, 63% of the responder $CD4^+$ cells in AMP-treated co-cultures were $CD4^+CD25^-Foxp3^+$ cells with similar percentages $CD152^+$ $GITR^+$, $CD152^+GITR^-$, $CD152^-GITR^+$ and $CD152^-GITR^+$ subsets.

AMPs constitutively produce modest amounts of soluble PGE-2, soluble HLA-G (HLA-G5), and cytosolic IDO, whereas sHLA-G5 and IDO were considerably higher after IFNγ-treatment (FIG. 3A). TGF-β1 was below the level of detection (data not shown). Up-regulation of mHLA-G1 on IFNγ-treated AMPs and AMP after 48 h of allo-MLR culture was confirmed by FACS analysis (FIG. 3B). mRNA transcripts for immune-modulating factors IDO, PGE-2, iNOS, and PD1L2 were significantly increased in AMPs following IFNγ treatment and during allo-MLR/AMP culture relative to untreated AMPs (FIG. 3C). Banas et al (17) demonstrated that AMPs cultured in a transwell culture system have no significant effect on allo T-cell proliferation. As shown in FIG. 3D, significant suppression of T cell proliferation was observed in cultures supplemented (1:10 ratio) with supernatant derived from 72 h alloMRL/AMP cultures, indicating that inhibition is mediated by both cell-cell contact and subsequently released soluble factors. Blocking studies using 20 μM indomethacin in allo-MLR/AMP cultures in a cell-to-cell contact culture setting were inconclusive as indomethacin alone was shown to significantly inhibit allo T-cell proliferation.

Figure 5:
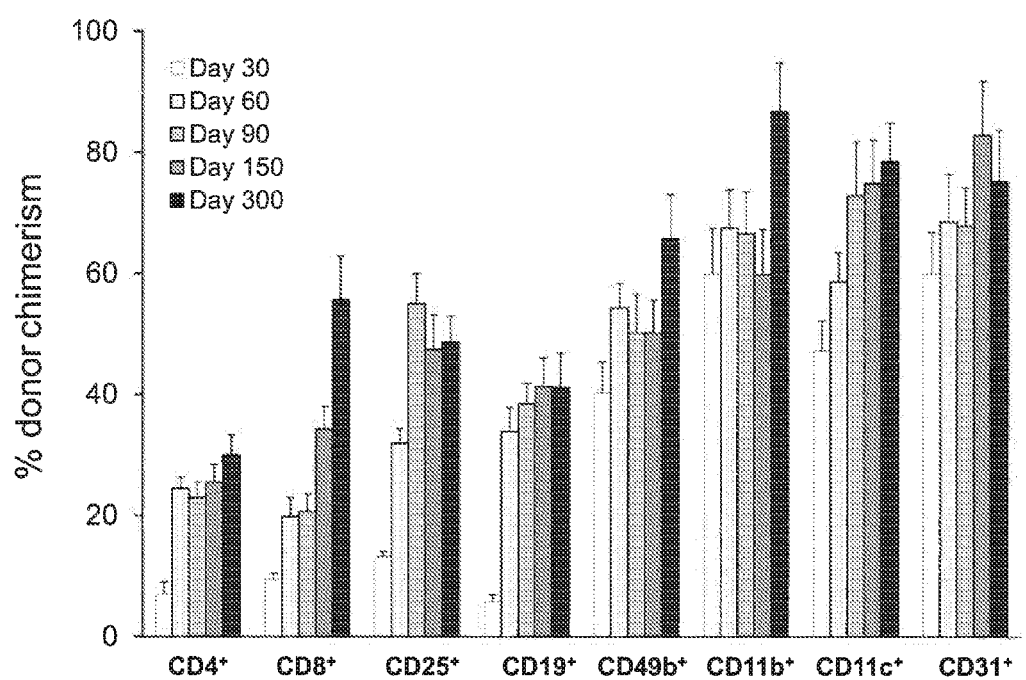
FIG. 5. Degree of stable multilineage hematopoietic cell macrochimerism in the peripheral blood. Donor hematopoietic chimerism (CD4$^+$ T-cells, CD8$^+$ T-cells, CD25$^+$ regulatory cells, CD19$^+$ B cells, CD49b$^+$ pan NK cells, CD11b$^+$ granulocyte-monocytes-macrophages, CD11c$^+$ dendritic cells and CD31$^+$ endothelial progenitor cells) was determined on days 30, 60, 90, 150, 300 after skin transplantation in the peripheral blood by multicolor flow cytometric analysis. Data points represent the mean±SD percent donor cell chimerism for each cell lineage (n=6/group).
Figure 6:
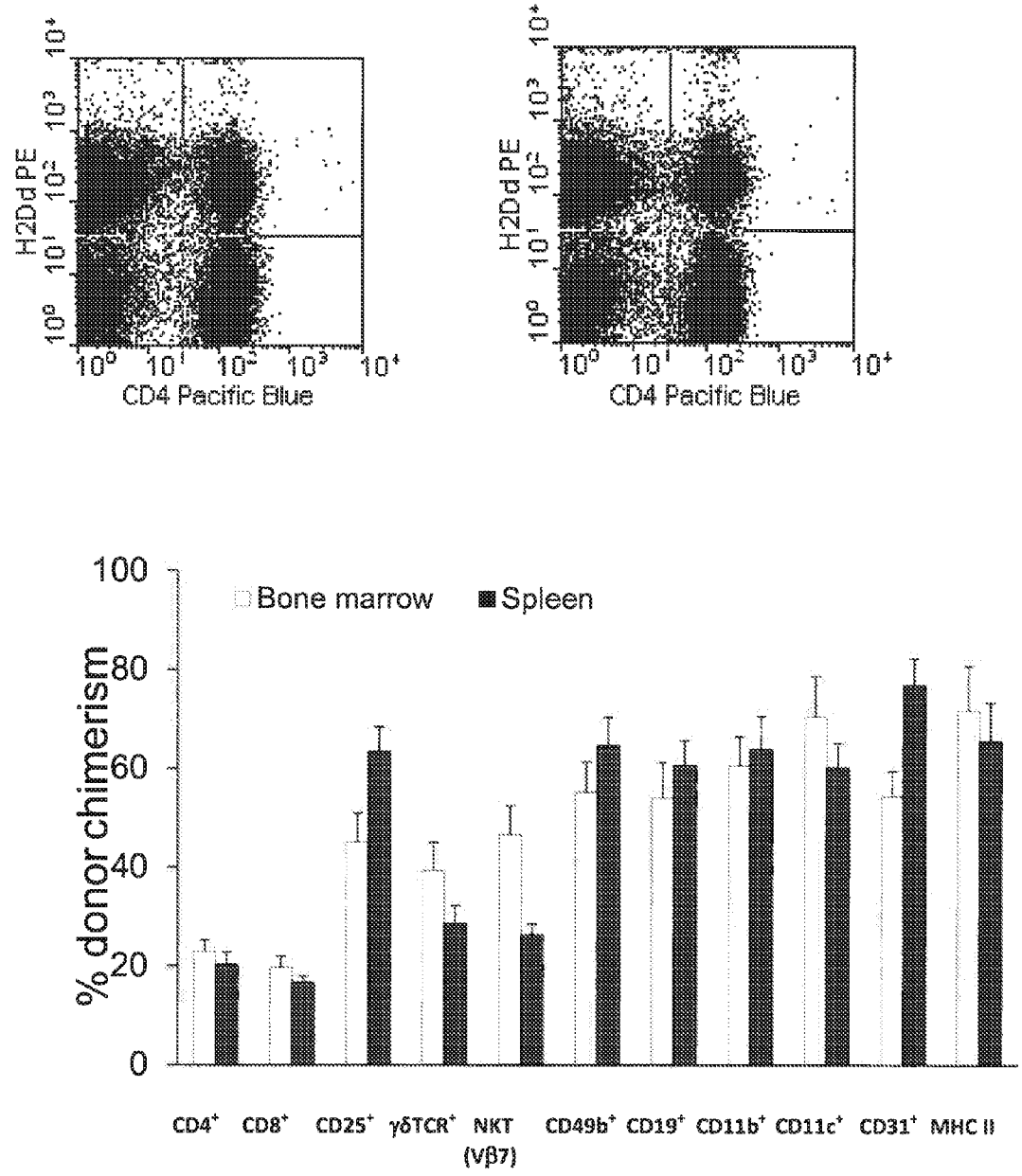
FIG. 6. The level and distribution of donor cell chimerism in the BM and spleen of allograft tolerant chimeric mice. C57BL/6 recipients received skin allografts (BALB/c, H-$2^d$) on day 0. Only treatment with CD4/CD8 mAb, low dose Bu, BMCs, and AMPs infusion promoted detectable chimerism (>1.0% donor cells) via flow cytometeric analysis. Data points represent the mean±SD for each lineage cell compartment at day 300 post skin grafting.

Administration of AMPs significantly prolonged allograft survival in the absence of donor BMCs (P<0.0001; n=22, MST 44 days; versus n=21, MST 29 days). Long-term acceptance (>300 days) of BALB/c derived skin grafts was achieved in 100% of mice that underwent the full conditioning protocol plus received AMPs+BMCs (n=13, FIG. 4A). Skin allografts on mice treated with AMPs alone, BMCs alone, and AMPs+BMCs without preconditioning were rapidly and robustly rejected (n=10, MST 12 days; n=10, MST 13 days, n=14, MST 13 days) with no evidence of macrochimerism (1%<circulating donor origin leukocytes). Control groups (no treatment, isotype controls) rapidly rejected donor allograft skin grafts (MST 10-13 days) (23). All mice in the preconditioned AMPs+BMCs treatment group established and maintained stable peripheral blood lymphoid and myeloid donor cell chimerism (22.4±3.8 to 46.9±7.9% $H-2^d$ cells at 30-300 days post skin transplantation; n=6, FIGS. 4B and 5). Flow cytometic analysis of splenocytes and BMCs from six chimeras on day 300 showed a similar level of donor chimerism observed among lymphoid and myeloid cell lineages (FIGS. 5 and 6).

Figure 4:
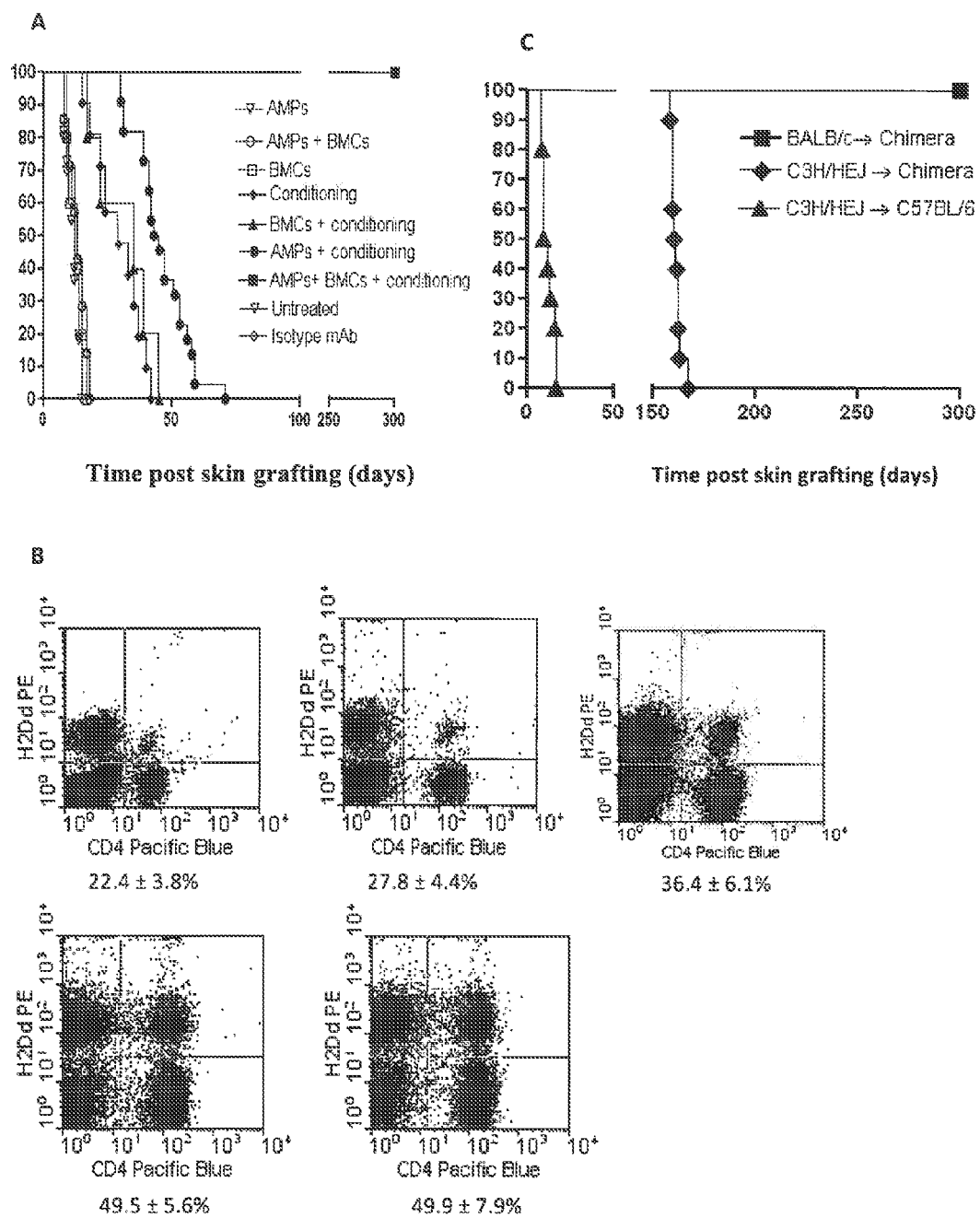
FIG. 4. Limited number of BMCs+AMPs induces indefinite skin allograft survival and mixed donor-recipient macrochimerism. Panel A. C57BL/6 (H-2b) recipients of BALB/c (H-2d) skin grafts received the following: 1) AMPs only treatment (n=10); 2) AMPs+BMC (n=14); 3) BMC only treatment (n=10); 4) cytoreduction condition only (n=22; anti-CD4/CD8 mAb therapy plus 5 mg/kg busulfan); 5) BMC+conditioning (n=10); 6) AMPs+conditioning (n=21); 7) AMPs+BMC+conditioning (n=13); 8) untreated (n=16); and 9) isotype control (n=12). Treatment of mice with anti-CD4/CD8 mAbs (10 mg/kg) occurred on day 0, +2, +5, +7, and +14 relative to skin grafting on day 0. Mice were treated with a single dose of busulfan (5 mg/kg). Control groups (no treatment, isotype controls) rapidly rejected donor allograft skin grafts (MST 10-13 days). Panel B. Percentage of donor derived cells (H-$2^d$) in the peripheral blood of allograft tolerant recipients measured 30, 60, 90, 150, and 300 days after graft transplantation (n=6 donor graft tolerant chimeric mice). Panel C. All chimeras accepted secondary donor-specific skin grafts (>150 days) and rejected third party grafts (C3H/HeJ, H-$2^k$) within 17 days; consistent with the rate of graft rejection when C3H/HEJ skin was grafted onto untreated normal C57BL/6 mice.

Placement of secondary donor BALB/c skin grafts on chimeric mice at 150 days were permanently accepted (FIG. 4C). In contrast, chimeras rejected MHC disparate third-party C3H/HeJ skin allografts in less than 17 days (n=10, MST 10.5 days), within a time course similar to non-chimeric untreated control mice.

Figure 7:
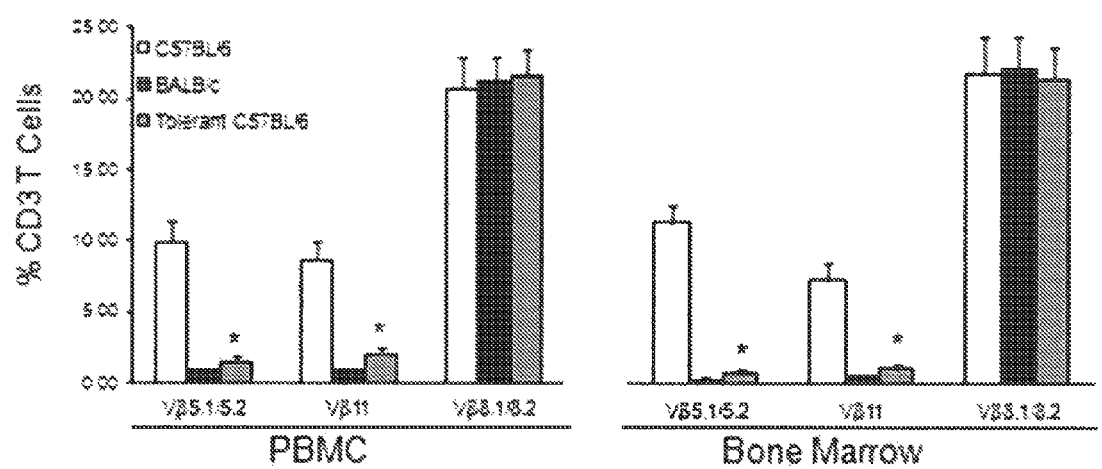
FIG. 7. Deletion of alloreactive T-cell clones expressing specific TCR Vβ families. Peripheral blood and BMC from chimeric and allograft recipient tolerant mice on day 300 post skin transplantation were stained with specific flurochome-conjugated Abs against CD3, Vβ5.1./5.2, Vβ8.1/8.2 and Vβ11 or isotype control Abs. The proportion of CD3$^+$ T-cells expressing each Vβ was determined by multicolor flow cytometry. Data points represent the mean±SD for each group (n=6). * $p<0.05$, significant difference compared with naïve C57BL/6 mice.

As shown in FIG. 7, $CD3^+$ T-cells from BALB/c ($H-2^d$, Thy1.2, $I-E^+$) donors do not express TCR-Vβ5.1/5.2 (0.9%) and TCR-Vβ11 (0.9%), whereas $CD3^+$ T cells from C57BL/5 ($H-2^b$, Thy1.2, $I-E^-$) recipients express TCR-Vβ5.1/5.2 (9.9%) and TCR-Vβ11 (8.7%) and comparable levels of TCR-Vβ8.1/8.2 (21%). BALB/c mice express I-E, which is required to present superantigens derived from endogenous retroviruses encoded in the BALB/c genome. T-cells expressing TCRs containing TCR Vβ5.1/5.2 or TCR-Vβ11, which can bind to these superantigens, are deleted in I-E positive BALB/c mice (and in chimeric C57BL/6 containing engrafted BALB/c cells after bone marrow transplantation), but not in C57BL/6 mice lacking I-E expression (25, 27). As shown in FIG. 7, a significant decrease in the percentage of TCR-Vβ5.1/5.2 and TCR-Vβ11 $CD3^+$ alloreactive host T-cells was observed in chimeras without any change in the percentage of non-alloreactive TCR-Vβ8.1/8.2 CD3+ T-cells in chimeric recipients, naive C57BL/6 hosts and BALB/c donors.

Figure 8:
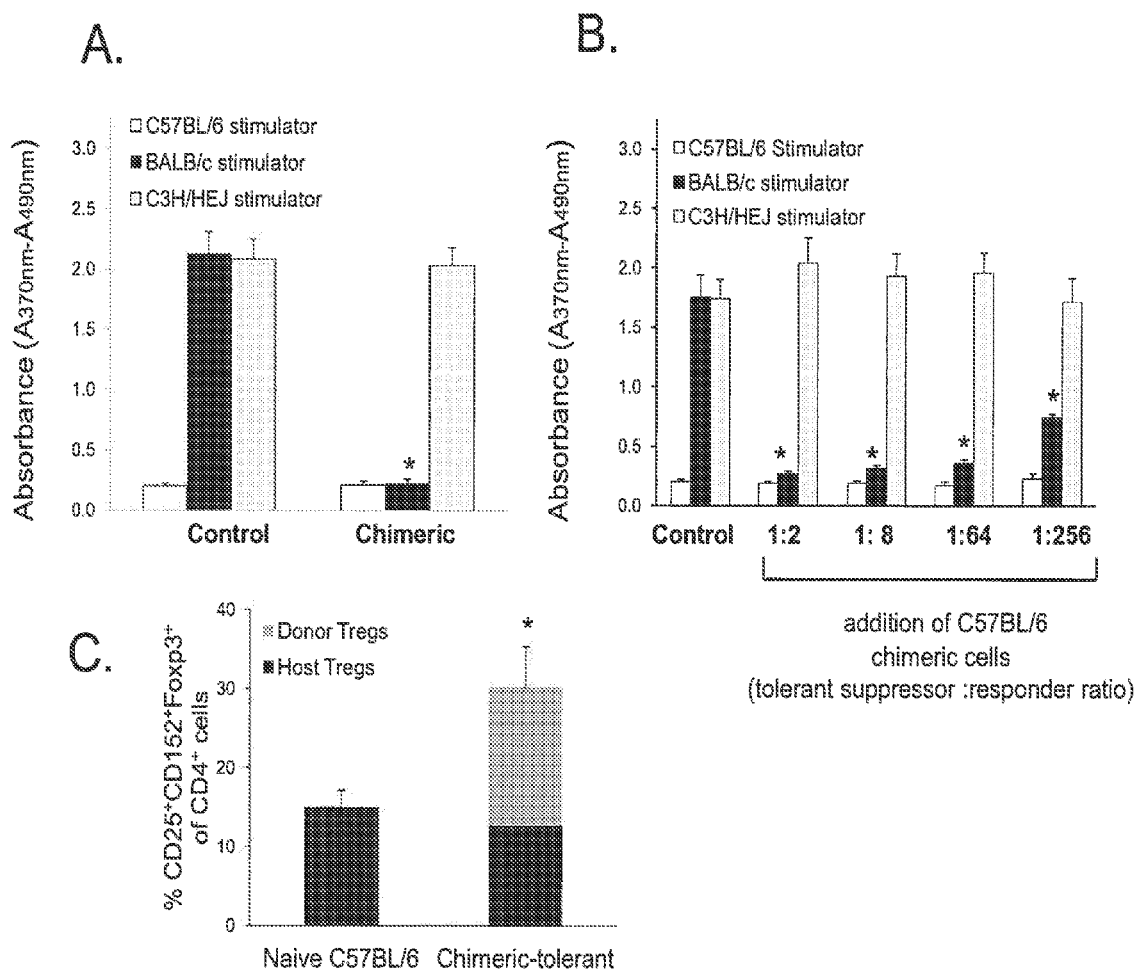
FIG. 8. ASCs were added to primary mixed lymphocyte reaction (MLR) cultures between C57BL/6 (responder cells) and irradiated BALB/c (stimulatory cells). ASC strongly suppressed alloreactive T-cell proliferation when added at the initiation of culture. In Panel (A), Splenocytes from chimeric-tolerant C57BL/6 recipient mice were cocultured with irradiated naïve C57BL/6, BALB/c and C3H/HeJ spelencoytes. After 4 days the co-cultures, the cells were pulsed for 18 h with BrdU, after which BrdU incorporation into newly synthesized DNA was measured. The data were expressed as the mean absorbance±SD. * $p<0.05$, significant difference compared with control group. In Panel (B) Naive C57BL/6 splenocytes ($5\times10^5$) were cocultured with the same number of irradiated naïve C57BL/6, naïve allogeneic BALB/c, or naïve allogenic C3H/HEJ spleen cells. To assess allospecifc regulatory function in vitro, equal numbers of irradiated splenocytes from tolerant recipient C57BL/6 mice were cocultured as third party regulatory cells at suppressor-to-responder cell ratio ranging from 1:1 to 1:256. After 4 days, the co-cultures were pulsed for 18 h with BrdU, after which BrdU incorporation into newly synthesized DNA was measured. In Panel (C), splenocytes isolated from naïve and chimeric-tolerant C57BL/6 mice (day 300 post allograft transplantation) were stained with anti-CD4-V500, anti-CD25-PE-CY7 and anti-Foxp3-PB and analyzed by flow cytometry. The frequency of each T-regulatory cell population is expressed as the mean±SD of three mice. * $p<0.05$ significant difference compared with naïve controls.

Lymphocytes in the spleen of chimeras at day 300 post skin grafting were functionally tolerant to host and donor-strain alloantigens, yet competent to respond to third-party alloantigens (FIG. 8A).

Splenocytes from chimeras at day 300 post skin grafting significantly inhibit allo-MLR antigen-specific T-cell responses in vitro in a dose dependent manner (FIG. 8B). The titration curve revealed a breakpoint at a suppressor-responder cell ratio of approximately 1:64. These results demonstrate that spleens of chimeric tolerant mice contain potent immunoregulatory suppressor cells. Chimeras had a significantly higher number of CD4+CD25+Foxp3+$T_{regs}$ amongst CD4+ T-cells (15.0%±2.1% vs. 30.2.9%±5.13% as compared to naïve controls). Among the CD4+CD25+Foxp3+ $T_{regs}$, 58.27%±5.0% were shown to be of donor origin.

Figure 9:
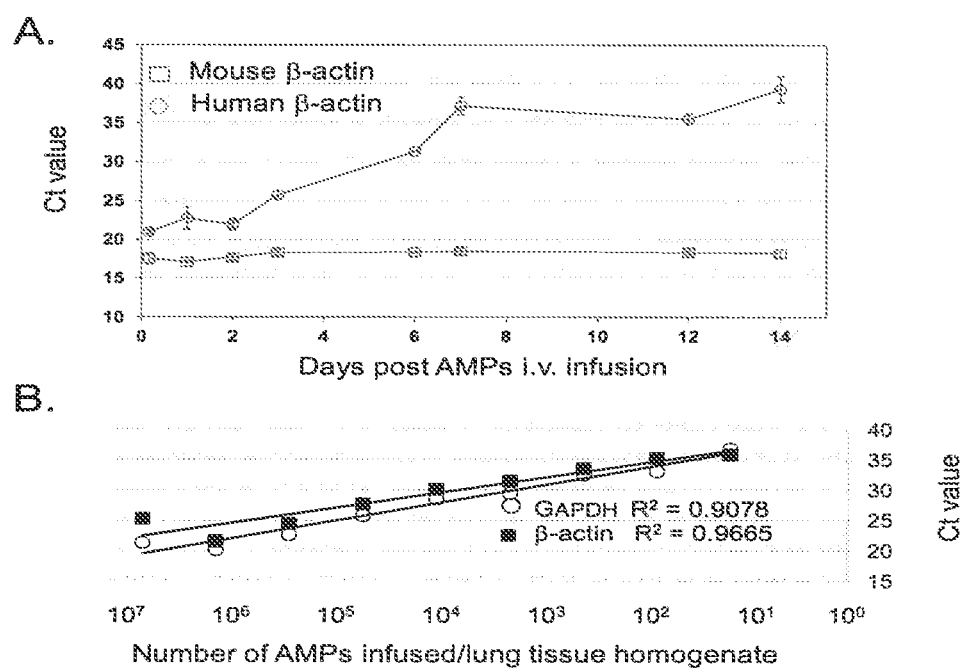
FIG. 9. Cell trafficking and biodistribution of AMPs following intravenous infusion in skin allograft transplanted mice treated with the full conditioning regimen. (A) Quantitatve RT-PCR analysis of human β-actin expression in lung tissues at various times post AMPs infusion (4 h and days 1, 2, 3, 6, 7, 12 and 14); results are shown relative to the mouse housekeeping gene beta-actin (muβactin). (B) Total lung tissue homogenate from control mice spiked with $5\times10^6$-13 AMPs prior to mRNA isolation showed an excellent linear correlation between AMPs cell numbers and human mRNA transcripts for housekeeping genes beta actin (huIa-actin) and glyceraldehyde-3-phosphate dehydrogenase (huGAPDH). Human gene transcripts from as few as 50 AMPs/lung tissue (1 μg RNA amplified) were easily detected using this spiking system. Gene transcripts with a Ct value ≥35 are considered not detectable.

The intravenous (i.v.) co-infusion of AMPs+BMC in skin transplanted mice resulted in entrapment of AMPs in lung tissue. AMPs persisted in the lung tissue for up to 6 days post infusion (FIG. 9A). Based on AMP spiking experiments, the detection of human β-actin and GAPDH was in the range of 25-50 cells per tissue/organ (FIG. 9B). mHLA G1 expression increased on lung entrapped AMPs at day 3 post AMP infusion (3.6% vs. 63.7%; MFI 142 vs 831; FIG. 9B). AMPs engraftment in the lungs at day-3 was confirmed by histological detection of 3-7 CFSE positive cells per 5 µm tissue section. Migration and redistribution to the spleen, thymus, liver, bone marrow, lymph node, mesenteric intestine, parietal peritoneum and within the skin margin and donor skin graft was not detectable by RT-PCR for human β-actin mRNA. Mouse mRNA transcripts for tumor necrosis factor (TNF-α)-induced protein 6 (TSG-6) increased 2.1-3.2 fold in both treatment groups. However mRNA transcripts for human IDO, sHLA-G5 and PGE-2 expression were undetectable. In comparison to naïve mice, the number of CD4+ splenocytes was reduced ~98% in both treatment groups due to the anti-CD4/CD8 mAb therapy. The proportion of resident CD4+CD25+Foxp3+CD152+ $T_{regs}$, in the spleen was greater in the AMP plus BMC treated mice with 20-30% of the cells GITR positive. Interestingly, most of the CD4+CD25−Foxp3+ cells in both treatment groups were CD152+ but GITR.

Also shown is the representative flow cytometric analysis showing mHLA-G1 expression on untreated AMP co-infusion (FIG. 10 (A)). Also shown is a representative flow cytometric analysis of splenic $T_{regs}$ (FIG. 10 (B)) at day 10 post skin grafting and day 3 post BMC and BMC plus AMP infusion.

As illustrated in this Example, it is demonstrate that a subset of human amnion epithelial cells (hAECs) termed Amnion-derived Multipotent Progenitor cells (AMPs) when used in concert with immunological conditioning (anti-CD4/CD8 mAb therapy plus low-dose non-myeloablative busulfan treatment), can promote engraftment of limiting numbers of donor bone marrow cells across MHC barriers, and lead to stable multilineage mixed-chimerism and tolerance to concurrently placed skin allografts without the need for long-term immunosuppression and development of graft versus host disease (GvHD). Furthermore, in the absence of BMCs, intravenous administration of AMPs under the coverage of cytoreduction led to a significant prolongation in skin graft survival in comparison to mice that received only the conditioning regimen. In contrast, treatment of conditioned mice with BMCs alone failed to prolong graft survival. Based on these findings AMPs may, therefore, be a pro-tolerogenic cellular therapeutic that could have clinical efficacy for both solid organ and hematopoietic stem cell transplant applications.

The role of donor T-cell chimerism and the production/maintenance of donor regulatory T-cells ($T_{regs}$) in the control of immune responsiveness have been clearly recognized in the prevention of allograft rejection (23, 25, 28, 29). Remarkably, we observed a comparable magnitude of stable chimerism with BMCs transplanted together with AMPs as achieved with 40-400 times as many BMCs transplanted with cytoreduction therapy alone (24, 30, 31). Our findings suggest both deletional and nondeletional mechanisms contributed to maintenance of allograft tolerance via deletion of alloreactive T-cell clones plus generation of potent suppressor T-cells and increased numbers CD4+CD25+FoxP3+ $T_{regs}$ wherein 58.27%±5.0% of the $T_{regs}$ were shown to be of donor origin. These results further substantiate the findings of Velasquez-Lopera et al (32) demonstrating that both recipient and donor-derived $T_{regs}$ play active roles in inhibiting T-cell alloreactivity.

As illustrated in this example, the functional in vivo immunomodulatory activity of AMPs must occur relatively quickly post infusion without the need for long term cell survival or engraftment. Others have shown mice treated with hAECs following bleomycin-induced lung injury reduced inflammation and attenuated cytokine expression resulting in decreased fibrosis without any significant engraftment of hAECs in injured lung, or other tissues (33) (34). Consistent with our findings, Liu et al (21) demonstrated that hAECs had long lasting immunosuppressive effects in a murine model of multiple sclerosis, were transiently detectable in the lung but not found in either the CNS or lymphoid tissues. Interestingly, we detected a 2-3 fold increase in mRNA transcript for mouse TSG-6 which others have shown has anti-inflammatory properties and tissue repair benefits (improved function and decreased scarring) when induced by MSC microemboli formation in the lungs (35-37).

Being of placental origin at the fetal-maternal interface, AMPs constitutively express low levels of the immunomodulatory mHLA-G1 (38), which we confirm can be increased with IFN-γ stimulation (17). Recently, it was shown that MSC-derived from human fetal liver demonstrated longer-lasting immunomodulatory properties compared to adult BM-MSC due to the expression of mHLA-G1, and were more efficient at inducing T-cell apoptosis and secretion of the immunosuppressive cytokine IL-10 (39). Roelen et al (40) reported similar differential immunomodulatory effects using fetal-derived multipotent MSCs in comparison to maternal-derived MSCs. Interestingly, we found that mHLA-G1 on AMPs is more pronounced and maintained at higher levels in vivo following their intravenous infusion. Furthermore, Liang et al (41, 42) who showed that intravenous infusion of sHLA-G coated microbeads prior to skin allograft transplantation induced prolonged graft survival tolerance though HLA-G Ig-like transcript (ILT) inhibitory receptors which have been shown to be differentially expressed by NK, T-cell, and antigen-presenting cells (43, 44) and lead to tolerogenic DC generation and subsequent attenuation of T-cell stimulation via a IL-6-STAT3 signaling pathway (44).

While HLA-G has been shown to inhibit T-cell proliferation, promote IFN-γ production, and expansion of CD4+CD25+Foxp3+ $T_{regs}$ (45) and several others hypothesize that HLA-G may play a immune regulatory role in solid organ transplants (heart, liver-kidney) (46-51) by dampening allograft inflammatory responses and providing an escape mechanism used by malignant cells to avoid immune surveillance (52). Therefore, HLA-G expression at the time of BMC transplantation and AMP infusion may be advantageous for xenogenic and allogeneic cells that are potential targets for cytotoxic effector cells, and be a potential immune escape mechanism in the short term.

The mechanisms by which AMPs promote immune regulation, stable multilineage macrochimerism and allograft tolerance have not been fully elaborated. We found AMP-mediated immunosuppression requires an initial cell-contact dependent mechanism involving direct interaction with other immune cells, the production of soluble factors derived from activated AMPs, differential cytokine production, and increases in the proportion of adaptive mature $CD4^+CD25^+Foxp3^+CD152^+$ and immature $CD4^+CD25^+Foxp3^+CD152^+$ $T_{regs}$ cells. During allo-MLR/AMP co-culture AMPs constitutively secrete and express increased mRNA transcripts for a number of key IFNγ inducible immunoregulatory molecules such as PGE-2, IDO, iNOS, PD1L2 and sHLA G5. These factors suppress T-cell and NK cell function either directly or indirectly though modulation of immature DCs (53, 54), support the expansion of adaptive $CD4^+CD25^+Foxp3^+$ $T_{regs}$ and play important roles as negative regulators in immune suppression and T-cell anergy (45, 55). Furthermore, we found that a modest amount of supernatant collected from allo-MRL/AMP co-cultures had profound suppressive effects on allo-MLR T-cell proliferation. Concordantly, supernatants from allo-MLR/AMP cultures contained ample amounts of IFNγ but undetectable level of IL-2. These findings suggest that the immunosuppressive effects of AMPs on T-cell proliferation in vitro, like some MSCs, appear to have both contact-dependent and contact-independent components involving the early production of IFN-γ by T-cells and possibly other immunosuppressive factors contained in the inflammatory milieu (40, 56-58). In general, we conclude that the immune modulatory properties of AMPs, like other MSC preparations, require priming by proinflammatory cytokines (56-58). Taken together, we speculate that our results are consistent with the described Th1↑→IFNγ→IDO→Th1← axis resulting in a negative feedback regulatory loop to self-limit Th1 responses, inhibit antigen-specific T-cell proliferation and cytotoxicity and promote the generation of $T_{regs}$ (59).

The induction of in vivo tolerance depends upon the two-way interaction between donor and host cells. The mechanism(s) involved in AMP-induced $T_{reg}$ development and how these adaptive regulatory cells exert their immunosuppressive effects in vitro and in vivo is unclear. Others have shown that MSC and AEC-mediated allosuppression involves $T_{reg}$ induction, a sequential process involving direct contact with $CD4^+$ cells, the production of immune regulatory suppressive factors (PGE-2, TGF β1, IL-10, IDO) and the modulation of DC differentiation and function (60-62). In our AMP co-culture system, neither TGF-β1 nor IL-10 appear to be involved in AMP mediated T-cell immunosuppression or $T_{reg}$ generation. Although conflicting data exist, PGE-2 has been shown to inhibit T-cell proliferation and IL-2 production, increase macrophage IL-10 production, induce Tregs and inhibit monocyte to DC differentiation (63). In contrast, others report PGE-2 can enhance allogeneic T-cell proliferation and antigen presentation through upregulation of co-stimulatory molecules on DC (64, 65). Our in vitro studies using indomethacin to block AMP-derived PGE-2 were inconclusive as allo-MLR T-cell proliferation alone was significantly inhibited. This result was unexpected and inconsistent with a recent study conducted by Liu et al (21) demonstrating indomethacin significantly counteracted hAEC-mediated suppression of T-cell activation.

Interestingly, as illustrated in this Example, AMP-treatment results in a marked increase in a $CD4^+CD25^-Foxp3^+$ $T_{reg}$ cell population, which expresses high level of both CD152 and GITR in the apparent absence of IL-2 production. IL-2 has been shown to be required for the development, expansion, and/or function of $CD4^+CD25^+$ $T_{regs}$, however when they undergo homeostatic expansion in vivo, they lose expression of CD25 but retain potent Treg functional activity (66, 67). Consequently, AMPs may exert their immunosuppressive function directly through release of regulatory mediators and/or amplified regulatory signaling. This is an interesting supposition given CD152/CTLA4 is a distinct signaling pathway capable of deleting activated T cells when TCR signaling is not accompanied by significant IL-2 (68). Therefore, one is tempted to hypothesize that AMP-induced Tregs may down regulate immune responses through direct interaction of membrane CD152 (CTLA4) with costimulatory molecules (CD80, CD86) on APCs/DCs leading to activation of IDO-induced Tregs resulting in increased catabolism of free extracellular tryptophan and accumulation of toxic tryptophan metabolites, and subsequent inhibition of T-cell proliferation (58, 62, 69).

Example 2

Use of Adipose-Derived Stem Cells (ASC) for Induction of Allograft Tolerance

The adipose-derived stems cells (ASC) were derived and isolated at LaCells Inc., New Orleans, La. The cells were isolated from fresh human subcutaneous adipose lipoaspirate according to published methods (70, 71), with some minor modifications and characterized as described in references (72-75). The lipoaspirate tissue was washed extensively with warm phosphate-buffered solution (PBS) to remove erythrocytes and then digested in PBS supplemented with 0.1% collagenase type I (Worthington Biochemical Corporation, Lakewood, N.J., USA), 1% bovine serum albumin (BSA) and 2 mM $CaCl2$ for 1 h at 37° C. Following room temperature centrifugation at 300 g and resuspension in stromal medium [Dulbecco's modified Eagle medium (DMEM)/Hams F-12 medium supplemented with 10% FBS (HYCLONE™, Logan, Utah, USA) and 1% antibiotic/antimycotic], the stromal vascular pellet was plated at a density of 35 mL lipoaspirate digest/T175 flask (0.2 mL/cm2). After 24 h of incubation at 37° C., 5% $CO_2$, the adherent cells were washed with warm PBS and maintained in stromal medium until 80-90% confluent. The adherent population was harvested by digestion with trypsin (0.05%)/ethylene diaminetetra acetic acid (EDTA; 1 mM) at 37° C. for 5 min, washed in stromal medium and replated at $5 \times 10^3$ ASC/cm2 (passage 1; P1) or used in flow cytometric analyzes or cryopreserved for future use and/or intravenous transplantaiton. After isolation, cells had minimally expressed the following phenotypic markers: $CD45^-$, $CD73^+$, $CD90^+$ and $CD105^+$.

Skin grafting was conducted as above. In the studies, full thickness trunk skin grafts, approximately 4 $cm^2$ from BALB/c and C3H/HEJ mice were transplanted onto the dorsal flanks of C57BL/6 recipient mice. The grafts were secured with an adhesive bandage for 7 days.

Immunoconditioning is depicted (generally) in the diagram in FIG. 1. Five doses of a cocktail of CD4-α (YTS 191.1, 10 mg/Kg) and CD8-α mAbs (YTS 169.4, 10 mg/Kg)

were administered (i.p) on day 0, +2, +5, +7, and +14 relative to skin grafting on day 0 (23, 24). A single nonmyeloablative low dose of busulfan (5 mg/kg, i.p; Sigma-Aldrich) was given on day +5 (23). At day +7 post skin transplantation, donor bone marrow cells ($5 \times 10^5$) were infused i.v. with or without AMPs ($5 \times 10^6$ cells i.v. in D-PBS containing 100 U/ml preservative free heparin (Sigma-Aldrich) and 100 U/ml DNase containing 5 mM $Mg^{2+}$ (Worthington, Lakewood, N.J.). In addition, the impact of these treatments alone and in various combinations on the extent of chimerism and allograft survival was assessed. We found the addition of heparin and DNase in the infusion medium minimizes cellular aggregation and lethal pulmonary embolic events at the time of adipose-derived stem cell infusion. The results of these studies are depicted in FIGS. 11-13.

Figure 11:
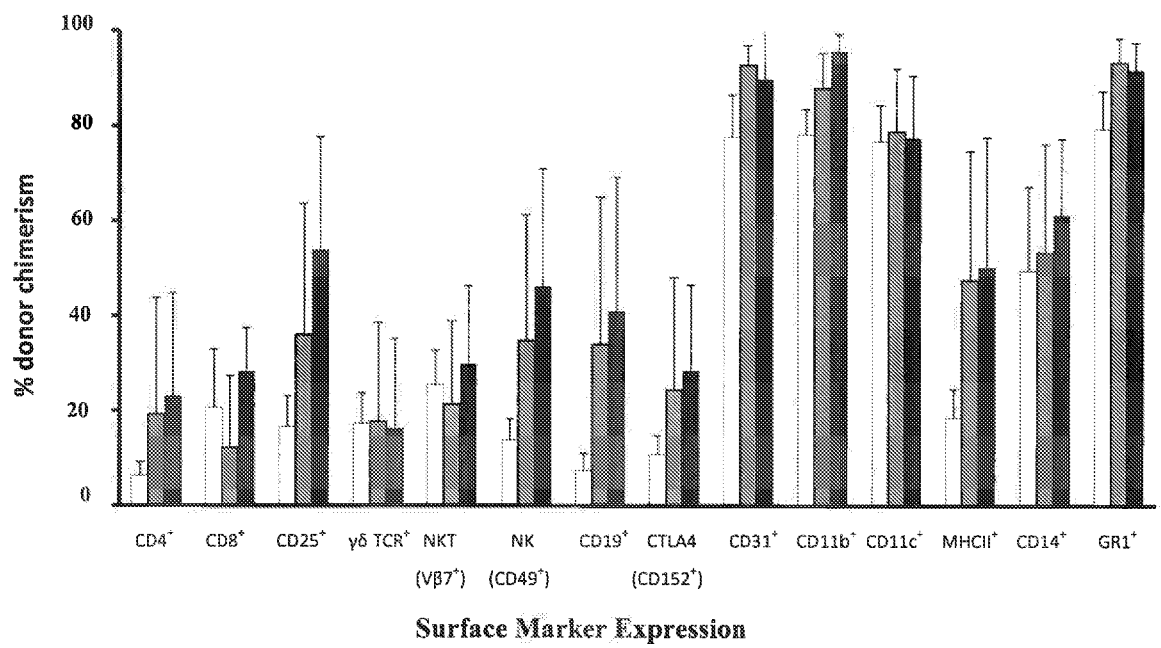
FIG. 11. Degree of stable multileneage hematopoietic cell macrochimerism in the peripheral blood following administration of adipose-derived stem cells and donor cells. Shown are flow cytometric analysis of specific cell markers of chimeric mice with time after skin graft. Flow cytometric analysis was conducted on peripheral blood from mice at 30, 60 and 90 days after skin grafts from BALB/c were transplanted onto C57BL/6 mice.

FIG. 11 illustrates the induction of stable multi-lineage lymphoid and myeloid hematopoietic chimerism 30 to 90 days after application of the tissue allograft and following anti-CD4/CD8 immunotherapy and intravenous co-infusion of limited numbers of unfractionated donor bone marrow plus adipose-derived stem cells. Shown in FIG. 11 is flow cytometric analysis of peripheral blood cell surface markers. The results indicate that the mice were chimeric, exhibiting 34-72% donor cells by day 90 in all lymphoid cell and myeloid cell types evaluated. Also illustrated in FIG. 11, chimerism was well established based on cell marker expression in T cells (CD4 and CD8), B cells (CD19), NK cells (CD49), as well as macrophages/monocytes, neutrophils and dentridic cell populations. The mice in FIG. 11 all accepted skin allografts from their marrow donors in the absence of any long-term immunosuppression. As such, the ASC play a key role in promoting the long-term stable donor cell chimerism.

Figure 12:
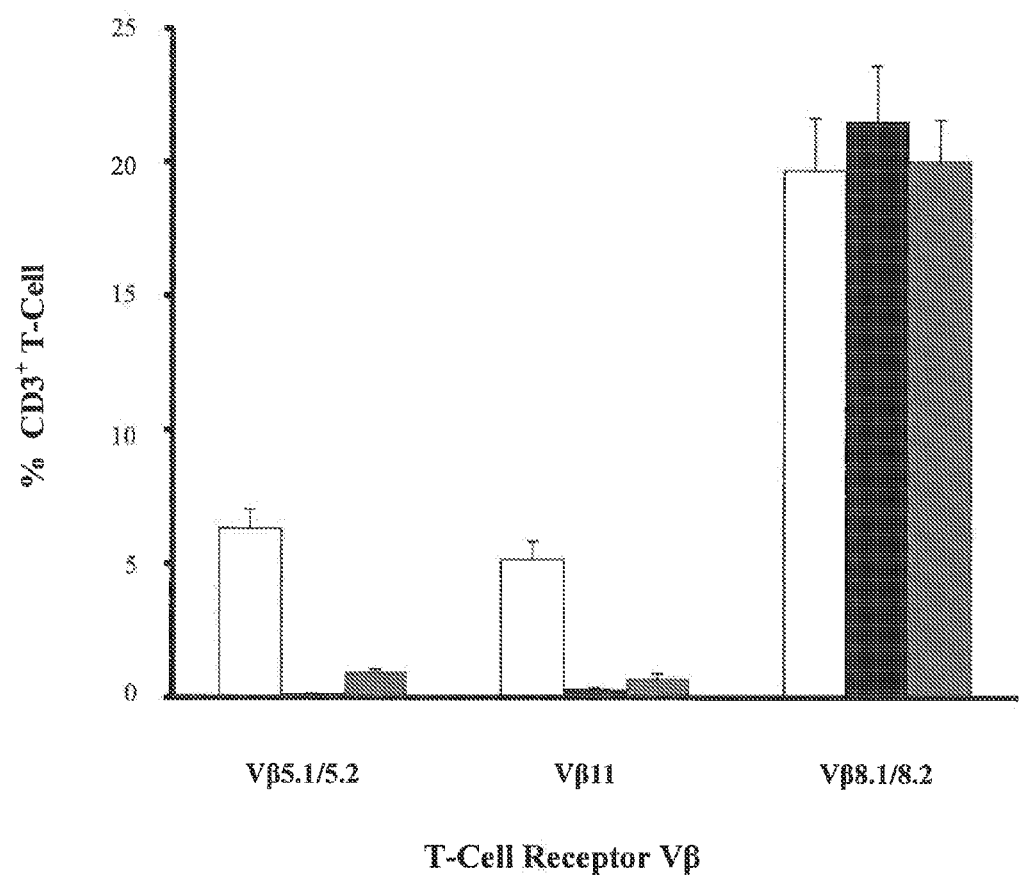
FIG. 12. Deletion of alloractive T-cell clones following administration of adipose-derived stem cells and donor cells. Peripheral blood and BMC from chimeric and allograft recipient tolerant mice on day 300 post skin transplantation were stained with specific flurochome-conjugated Abs against CD3, Vβ5.1./5.2, Vβ8.1/8.2 and Vβ11 or isotype control Abs. The proportion of CD3$^+$ T-cells expressing each Vβ was determined by multicolor flow cytometry. Data points represent the mean±SD for each group (n=6). * $p<0.05$, significant difference compared with naïve C57BL/6 mice.
Figure 13:
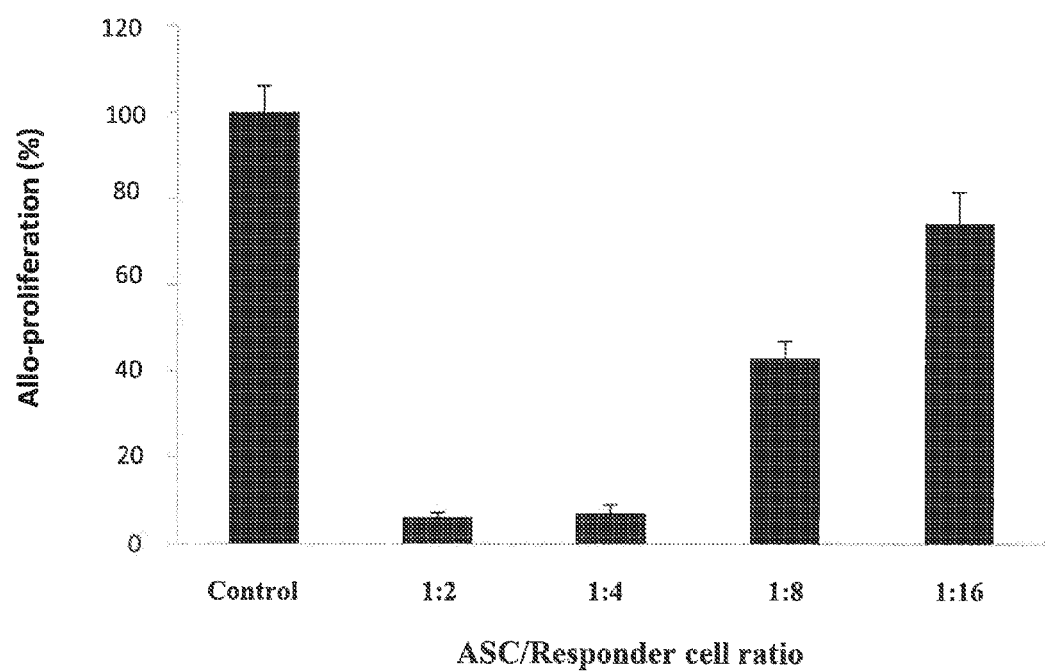
FIG. 13. Adipose stem cells (ASC) inhibit allo-MLR lymphocyte proliferation. Naive C57BL/6 splenocytes (as responder cells) were cultured 1:1 with irradiated (3 Gy) naïve BALB/c stimulatory cells. ASCs were added to the MLR at the onset of culture at the indicated ASC to responder cell ratios. Cell proliferation was analyzed by $^3$H-thymidine incorporation during the last 18 h of a 5 day culture. Results are expressed as the mean percent alloproliferation of quadruplicate cultures. Control represents only responder (C57BL/6) and irradiated stimulatory cells (BALB/c). Data are representative of two independent experiments.

The reduction of alloreactive T cells in chimeric skin allograft recipient mice, following anti-CD4/CD8 immunotherapy and intravenous co-infusion of limited numbers of unfractionated donor bone marrow plus ASC is illustrated in FIG. 12. In this study, the extent of deletion of T cells reactive to the MHC Class II antigen I-E (an important transplantation antigen) was determined by flow cytometry using anti-CD3 and the monoclonal antibodies specific for Vβ5.1/5.2 or Vβ11 T-cell receptor. As illustrated in FIG. 12, transplantation of limited numbers of I-E$^+$ donor unfractioned bone marrow plus ASC resulted in significant deletion of Vβ5.1/5.2 or Vβ11 CD3$^+$ alloractive T-cells in the peripheral blood of allograft teolerant chimeric mice. Therefore, these results indicate that in vivo infusion of ASC can significant modulate in vivo alloreactivity. Removal of the alloreactive cells was either through thymic deletion or deletion/anergy in the periphery in the chimeric mice (skin allograft recipients).

In order to determine whether human ASC could suppress a T cell response, ASC were included in a mixed lymphocyte response analysis, in vitro. In this study, ASCs were added to primary cultures of C57BL/6 responder cells and irradiated BALB/c stimulator cells. The results of the study are shown in FIG. 13 where ASC strongly suppressed, in a dose-dependent fashion, alloreactive T-cell proliferation. At the 1:2 ASC/responder ratio, greater than 90% of the alloreactivity was suppressed. Therefore, the results show that ASC have a significant immunosuppressive effect on T-cell alloreactivity.

Example 3

Method for Induction of Allograft Tolerance and Chimerism

The method provides a means for survival of allografts or transplanted tissue through the administration of human stem/progenitor-like cells. The inventive method contemplates the use of stem/progenitor-like cells derived from any number of cell types or possessing any number of cellular lineages. The important property is that they be capable of differentiating into multiple cell types and functions. Illustrations of types of stem/progenitor-like cells that can be used in the inventive method are given in Examples 1 and 2, which include amnion-derived stem cells and adipose-derived stem cells.

The inventive method provides a means of treating or reducing immunological and hematopoietic disease, including transplantation rejection, end organ failure, skin transplants, hematopoietic cell transplants, allograft rejection, inflammatory diseases of the skin, composite tissue transplantation, malignancies (i.e., cancer), hematologic diseases, immunodeficiencies, congenital diseases and autoimmune diseases. The method can also be used to treat patients who have been exposed to agents, toxins or radiation capable of marrow ablation. As such, the method can be used for bone marrow hematopoietic reconstitution. The inventive method can comprise graft transplantation of tissues or organs that are autologous, allogeneic, xenogenic, or chimeric to the individual being treated. An aspect of the current inventive method but that the immune system is not systemically suppressed.

The inventive method comprises the administration of stem/progenitor-like cells concomitant or shortly prior to or after the administration of donor bone marrow cells, wherein the donor bone marrow cells are immunologically compatible with the anticipated transplanted organ or tissue. As an example, donor cells and transplanted organ or tissue are immunological compatibility if donor cells and cells from transplanted organ or tissues are non-responsive in mixed lymphocyte reactions (MLR).

In an embodiment, the method comprises administration of stem/progenitor-like cells, such as adipose-derived stem cells, and donor cells in order to induce allograft tolerance. In one example, the stem/progenitor-like cells are co-administered at the same time. However, the inventive method also contemplates administering the progenitor cells before or after the administration of donor cells.

Other embodiments comprise administration of the stem/progenitor-like cells (e.g., ASC) and donor cells, in one or more doses, before or after allograft or tissue transplantation. In one embodiment, the progenitor cells and donor cells are administered up to ten (10) days, before or after the administration of organ or tissue transplantation. As an example, administration of stem/progenitor-like cells and donor cells are administered within 7 days post skin grafting. In another example, administration of stem/progenitor-like cells and donor cells are administered long before administration of an allograft or transplant tissue, for example, one year or more prior to transplantation.

The inventive method contemplates the use of donor cells, which are unfractionated cells derived bone marrow. The sources of the donor cells can be from cadavers or other cell libraries. In this embodiment, donor cells are administered, as described above, before, after or simultaneous to administration of stem/progenitor-like cells.

Doses of stem/progenitor-like cells are typically from $2-10 \times 10^7$ cells/kg. The stem/progenitor-like cells can be administered prior to or after multiple in vitro culture passages for expansion. Administration of cellular components can be administered intravenously, subcutaneously or intradermally.

The donor cells can consist of cells derived from or that have a variety of characteristics. For example, the donor cells can be stem cells, committed progenitor cells or differentiated cells. The donor cells can be unprocessed bone marrow, low density bone marrow cells, lineage negative bone marrow cells, hematopoietic stem/progenitor cells ($CD34^+$), and side population stem cells, Similarly, for cord blood and mobilized stem cells. Bone marrow cells, for example, can be derived from cord blood, vertebral body bone marrow cells, marrow cells isolated from ribs, iliac crest, long bones, umbilical cord blood, or mobilized stem cells.

As above, it is contemplated that human stem/progenitor-like cells can be from a number of sources, including, but not limited to: mesenchymal stem cells, adipose-derived stem cells, cord blood stem cells, placental stem cells, bone marrow cells, circulating peripheral blood stem cells, and cytokine mobilized stem cells. Human bone marrow cells can be derived from any source.

Adipose-derived cells can be isolated by any number of means. As an example, they can be isolated from human subcutaneous adipose lipoaspirate according to published methods (72-75), by washing the lipoaspirate tissue extensively with warm phosphate-buffered solution (PBS) to remove erythrocytes and then digested in PBS supplemented with 0.1% collagenase type I (Worthington Biochemical Corporation, Lakewood, N.J., USA), 1% bovine serum albumin (BSA) and 2 mM CaCl2 for 1 h at 37° C. Following room temperature centrifugation at 300 g and resuspension in stromal medium (Dulbecco's modified Eagle medium (DMEM)/Hams F-12 medium supplemented with 10% FBS (Hyclone, Logan, Utah, USA) and 1% antibiotic/antimycotic), the stromal vascular pellet was plated at a density of 35 mL lipoaspirate digest/T175 flask (0.2 mL/cm2). After 24 h of incubation at 37° C., 5% $CO_2$, the adherent cells were washed with warm PBS and maintained in stromal medium until 80-90% confluent. The adherent population was harvested by digestion with trypsin (0.05%)/ethylene diaminetetra acetic acid (EDTA; 1 mM) at 37° C. for 5 min, washed in stromal medium and replated at $5 \times 10^3$ ASC/cm2 (passage 1; P1) or used in flow cytometric analyzes or cryopreserved for future use and/or intravenous transplantation. After isolation, cells had minimally expressed the following phenotypic markers: $CD45^-$, $CD73^+$, $CD90^+$ and $CD105^+$.

In one embodiment, the inventive method comprises immune-conditioning, wherein $CD4^+$ and $CD8^+$ cells are depleted. Depletion of $CD4^+$ and $CD8^+$ cells can be conducted by any means, including, in a preferred embodiment, by administration of one or more doses (1 to 10 mg/kg) of anti-$CD4^+$ and anti-$CD8^+$ cells antibody. In a preferred embodiment, immune-conditioning is conducted prior to administration of donor cells.

Additionally, one or more doses of nonmyeloablative low dose of chemotherapeutic agents, for example anti-neoplastic agents, are administered, preferably prior to or concomitant to administration of donor cells. An illustrative example of a contemplated anti-neoplastic agents includes alkylating anti-neoplastic agents, for example the alkylating neoplastic agent busulfan. In a preferred embodiment, busulfan is administered at a single dose of 5 mg/kg one to two days prior to administration of AMPs and donor cells.

Embodied in the inventive method is a means for expansion of pre-existing $T_{reg}$ cell population of the donor and/or host. Also embodied in the method is the establishment of a stable donor cell multilineage cell chimerism. Additionally, one embodiment is the expression of human leukocyte antigen G (i.e., HLA-G) wherein HLA-G may enhance xenogenic and allogenic tolerance. A further embodiment is induction of tolerance by increases in the proportion of adaptive mature $CD4^+CD25^+Foxp3^+CD152^+$and immature $CD4^+CD25^+Foxp3^+CD152^+T_{regs}$ cells. A further embodiment is the induction of allograft tolerance by the expression of IFNγ-inducible immunoregulatory molecules such as PGE-2, Indoleamine 3,5-dioxygenase-1 (IDO-1), inducible nitric oxide synthetase (iNOS), PD1L2 and sHLA-G5 or other factors that suppress T-cell and NK cell function either directly or indirectly through modulation of immature dendritic cells and expansion of $CD4^+CD25^+Foxp3^+$ $T_{regs}$.

REFERENCES

1. Webber A, Hirose R, Vincenti F. Novel strategies in immunosuppression: issues in perspective. Transplantation. 2011; 91(10):1057-64. Epub 2011 Mar. 18.
2. Girlanda R, Kirk A D. Frontiers in nephrology: immune tolerance to allografts in humans. Journal of the American Society of Nephrology: JASN. 2007; 18(8):2242-51. Epub 2007 Jul. 20.
3. Rothstein D M. Immunosuppression and regulation: cast in new light? Journal of the American Society of Nephrology: JASN. 2006; 17(10):2644-6. Epub 2006 Sep. 15.
4. Ferrer I R, Wagener M E, Song M, Kirk A D, Larsen C P, Ford M L. Antigen-specific induced Foxp3+ regulatory T cells are generated following CD40/CD154 blockade. Proceedings of the National Academy of Sciences of the United States of America. 2011; 108(51):20701-6. Epub 2011 Dec. 7.
5. Newell K A. Clinical transplantation tolerance. Seminars in immunopathology. 2011; 33(2):91-104. Epub 2011 Feb. 18.
6. Page A, Srinivasan S, Singh K, Russell M, Hamby K, Deane T, et al. CD40 blockade combines with CTLA4Ig and sirolimus to produce mixed chimerism in an MHC-defined rhesus macaque transplant model. American journal of transplantation: official journal of the American Society of Transplantation and the American Society of Transplant Surgeons. 2012; 12(1):115-25. Epub 2011 Sep. 21.
7. Kirk A D. Clinical tolerance 2008. Transplantation. 2009; 87(7):953-5. Epub 2009 Apr. 9.
8. Parolini O, Soncini M, Evangelista M, Schmidt D. Amniotic membrane and amniotic fluid-derived cells: potential tools for regenerative medicine? Regenerative medicine. 2009; 4(2):275-91. Epub 2009 Mar. 26.
9. Soncini M, Vertua E, Gibelli L, Zorzi F, Denegri M, Albertini A, et al. Isolation and characterization of mesenchymal cells from human fetal membranes. Journal of tissue engineering and regenerative medicine. 2007; 1(4): 296-305. Epub 2007 Nov. 27.
10. Manuelpillai U, Moodley Y, Borlongan C V, Parolini O. Amniotic membrane and amniotic cells: potential therapeutic tools to combat tissue inflammation and fibrosis? Placenta. 2011; 32 Suppl 4:S320-5. Epub 2011 May 17.
11. Cargnoni A, Di Marcello M, Campagnol M, Nassuato C, Albertini A, Parolini O. Amniotic membrane patching promotes ischemic rat heart repair. Cell transplantation. 2009; 18(10):1147-59. Epub 2009 Aug. 5.
12. Cargnoni A, Ressel L, Rossi D, Poli A, Arienti D, Lombardi G, et al. Conditioned medium from amniotic mesenchymal tissue cells reduces progression of bleomycin-induced lung fibrosis. Cytotherapy. 2012; 14(2):153-61. Epub 2011 Oct. 1.
13. Cargnoni A, Gibelli L, Tosini A, Signoroni P B, Nassuato C, Arienti D, et al. Transplantation of allogeneic and xenogeneic placenta-derived cells reduces bleomycin-induced lung fibrosis. Cell transplantation. 2009; 18(4): 405-22. Epub 2009 Jul. 23.
14. Chen Z, Tortella F C, Dave J R, Marshall V S, Clarke D L, Sing G, et al. Human amnion-derived multipotent progenitor cell treatment alleviates traumatic brain injury-induced axonal degeneration. Journal of neurotrauma. 2009; 26(11):1987-97. Epub 2009 Nov. 6.
15. Tsuji H, Miyoshi S, Ikegami Y, Hida N, Asada H, Togashi I, et al. Xenografted human amniotic membrane-derived mesenchymal stem cells are immunologically tolerated and transdifferentiated into cardiomyocytes. Circulation research. 2010; 106(10):1613-23. Epub 2010 May 29.
16. Zhang D, Jiang M, Miao D. Transplanted human amniotic membrane-derived mesenchymal stem cells ameliorate carbon tetrachloride-induced liver cirrhosis in mouse. PloS one. 2011; 6(2):e16789. Epub 2011 Feb. 18.
17. Banas R A, Trumpower C, Bentlejewski C, Marshall V, Sing G, Zeevi A. Immunogenicity and immunomodulatory effects of amnion-derived multipotent progenitor cells. Human immunology. 2008; 69(6):321-8. Epub 2008 Jun. 24.
18. Wolbank S, Peterbauer A, Fahrner M, Hennerbichler S, van Griensven M, Stadler G, et al. Dose-dependent immunomodulatory effect of human stem cells from amniotic membrane: a comparison with human mesenchymal stem cells from adipose tissue. Tissue engineering. 2007; 13(6):1173-83. Epub 2007 May 24.
19. Magatti M, De Munari S, Vertua E, Gibelli L, Wengler G S, Parolini O. Human amnion mesenchyme harbors cells with allogeneic T-cell suppression and stimulation capabilities. Stem cells. 2008; 26(1):182-92. Epub 2007 Jul. 29.
20. Magatti M, De Munari S, Vertua E, Nassauto C, Albertini A, Wengler G S, et al. Amniotic mesenchymal tissue cells inhibit dendritic cell differentiation of peripheral blood and amnion resident monocytes. Cell transplantation. 2009; 18(8):899-914. Epub 2009 Jun. 16.
21. Liu Y H, Vaghjiani V, Tee J Y, To K, Cui P, Oh D Y, et al. Amniotic epithelial cells from the human placenta potently suppress a mouse model of multiple sclerosis. PloS one. 2012; 7(4):e35758. Epub 2012 May 9.
22. Steed D L, Trumpower C, Duffy D, Smith C, Marshall V, Rupp R, et al. Amnion-derived cellular cytokine solution: a physiological combination of cytokines for wound healing. Eplasty. 2008; 8:el 8. Epub 2008 May 8.
23. Anam K, Amare M F, Zins S R, Davis T A. Infusion of Lin-bone marrow cells results in multilineage macrochimerism and skin allograft tolerance in minimally conditioned recipient mice. Transplant immunology. 2010; 24(1):69-75. Epub 2010 Oct. 19.
24. Anam K, Akpinar E, Craighead N, Black A T, Hale D A. Targeted T-cell depletion or CD154 blockade generates mixed hemopoietic chimerism and donor-specific tolerance in mice treated with sirolimus and donor bone marrow. Transplantation. 2004; 78(9):1290-8. Epub 2004 Nov. 19.
25. Pilat N, Baranyi U, Klaus C, Jaeckel E, Mpofu N, Wrba F, et al. Treg-therapy allows mixed chimerism and transplantation tolerance without cytoreductive conditioning. American journal of transplantation: official journal of the American Society of Transplantation and the American Society of Transplant Surgeons. 2010; 10(4):751-62. Epub 2010 Feb. 13.
26. Dyson P J, Knight A M, Fairchild S, Simpson E, Tomonari K. Genes encoding ligands for deletion of V beta 11 T cells cosegregate with mammary tumour virus genomes. Nature. 1991; 349(6309):531-2. Epub 1991 Feb. 7.
27. Bill J, Kanagawa O, Woodland D L, Palmer E. The MHC molecule I-E is necessary but not sufficient for the clonal deletion of V beta 11-bearing T cells. The Journal of experimental medicine. 1989; 169(4):1405-19. Epub 1989 Apr. 1.
28. Domenig C, Sanchez-Fueyo A, Kurtz J, Alexopoulos S P, Mariat C, Sykes M, et al. Roles of deletion and regulation in creating mixed chimerism and allograft tolerance using a nonlymphoablative irradiation-free protocol. Journal of immunology. 2005; 175(1):51-60. Epub 2005 Jun. 24.
29. Xu H, Chilton P M, Huang Y, Schanie C L, Ildstad S T. Production of donor T cells is critical for induction of donor-specific tolerance and maintenance of chimerism. Journal of immunology. 2004; 172(3):1463-71. Epub 2004 Jan. 22.
30. Akpinar E, Craighead N, Smoot D, Hale D A. Potent skin allograft survival prolongation using a committed progenitor fraction of bone marrow in mice. Transplantation. 2004; 78(3):383-91. Epub 2004 Aug. 19.
31. Wells A D, Li X C, Li Y, Walsh M C, Zheng X X, Wu Z, et al. Requirement for T-cell apoptosis in the induction of peripheral transplantation tolerance. Nature medicine. 1999; 5(11):1303-7. Epub 1999 Nov. 5.
32. Velasquez-Lopera M M, Eaton V L, Lerret N M, Correa L A, Decresce R P, Garcia L F, et al. Induction of transplantation tolerance by allogeneic donor-derived CD4(+)CD25(+)Foxp3(+) regulatory T cells. Transplant immunology. 2008; 19(2):127-35. Epub 2008 May 28.
33. Hodges R J, Lim R, Jenkin G, Wallace E M. Amnion epithelial cells as a candidate therapy for acute and chronic lung injury. Stem cells international. 2012; 2012: 709763. Epub 2012 May 12.
34. Murphy S, Lim R, Dickinson H, Acharya R, Rosli S, Jenkin G, et al. Human amnion epithelial cells prevent bleomycin-induced lung injury and preserve lung function. Cell transplantation. 2011; 20(6):909-23. Epub 2010 Nov. 26.
35. Lee R H, Pulin A A, Seo M J, Kota D J, Ylostalo J, Larson B L, et al. Intravenous hMSCs improve myocardial infarction in mice because cells embolized in lung are activated to secrete the anti-inflammatory protein TSG-6. Cell stem cell. 2009; 5(1):54-63. Epub 2009 Jul. 3.
36. Danchuk S, Ylostalo J H, Hossain F, Sorge R, Ramsey A, Bonvillain R W, et al.
Human multipotent stromal cells attenuate lipopolysaccharide-induced acute lung injury in mice via secretion of tumor necrosis factor-alpha-induced protein 6. Stem cell research & therapy. 2011; 2(3):27. Epub 2011 May 17.
37. Doom J, Moll G, Le Blanc K, van Blitterswijk C, de Boer J. Therapeutic applications of mesenchymal stromal cells: paracrine effects and potential improvements. Tissue engineering Part B, Reviews. 2012; 18(2):101-15. Epub 2011 Oct. 15.
38. Carosella E D, Moreau P, Le Maoult J, Le Discorde M, Dausset J, Rouas-Freiss N. HLA-G molecules: from maternal-fetal tolerance to tissue acceptance. Advances in immunology. 2003; 81:199-252. Epub 2004 Jan. 9.
39. Giuliani M, Fleury M, Vernochet A, Ketroussi F, Clay D, Azzarone B, et al. Long-lasting inhibitory effects of fetal liver mesenchymal stem cells on T-lymphocyte proliferation. PloS one. 2011; 6(5):e19988. Epub 2011 Jun. 1.
40. Roelen D L, van der Mast B J, in't Anker P S, Kleijburg C, Eikmans M, van Beelen E, et al. Differential immunomodulatory effects of fetal versus maternal multipotent stromal cells. Human immunology. 2009; 70(1):16-23. Epub 2008 Nov. 18.
41. Liang S, Horuzsko A. Mobilizing dendritic cells for tolerance by engagement of immune inhibitory receptors for HLA-G. Human immunology. 2003; 64(11):1025-32. Epub 2003 Nov. 7.
42. Liang S, Ristich V, Arase H, Dausset J, Carosella E D, Horuzsko A. Modulation of dendritic cell differentiation by HLA-G and ILT4 requires the IL-6-STAT3 signaling pathway. Proceedings of the National Academy of Sciences of the United States of America. 2008; 105(24): 8357-62. Epub 2008 Jun. 14.
43. Naji A, Durrbach A, Carosella E D, Rouas-Freiss N. Soluble HLA-G and HLA-G1 expressing antigen-presenting cells inhibit T-cell alloproliferation through ILT-2/ILT-4/FasL-mediated pathways. Human immunology. 2007; 68(4):233-9. Epub 2007 Apr. 3.
44. LeMaoult J, Zafaranloo K, Le Danff C, Carosella E D. HLA-G up-regulates ILT2, ILT3, ILT4, and KIR2D L4 in antigen presenting cells, N K cells, and T cells. FASEB journal: official publication of the Federation of American Societies for Experimental Biology. 2005; 19(6):662-4. Epub 2005 Jan. 27.
45. Selmani Z, Naji A, Zidi I, Favier B, Gaiffe E, Obert L, et al. Human leukocyte antigen-G5 secretion by human mesenchymal stem cells is required to suppress T lymphocyte and natural killer function and to induce CD4+CD25highFOXP3+ regulatory T cells. Stem cells. 2008; 26(1):212-22. Epub 2007 Oct. 13.
46. Lila N, Amrein C, Guillemain R, Chevalier P, Latremouille C, Fabiani J N, et al. Human leukocyte antigen-G expression after heart transplantation is associated with a reduced incidence of rejection. Circulation. 2002; 105(16):1949-54. Epub 2002 May 9.
47. Deschaseaux F, Delgado D, Pistoia V, Giuliani M, Morandi F, Durrbach A. HLA-G in organ transplantation: towards clinical applications. Cellular and molecular life sciences: CMLS. 2011; 68(3):397-404. Epub 2010 Nov. 26.
48. Le Rond S, Azema C, Krawice-Radanne I, Durrbach A, Guettier C, Carosella E D, et al. Evidence to support the role of HLA-G5 in allograft acceptance through induction of immunosuppressive/regulatory T cells. Journal of immunology. 2006; 176(5):3266-76. Epub 2006 Feb. 24.
49. Creput C, Durrbach A, Menier C, Guettier C, Samuel D, Dausset J, et al. Human leukocyte antigen-G (HLA-G) expression in biliary epithelial cells is associated with allograft acceptance in liver-kidney transplantation. Journal of hepatology. 2003; 39(4):587-94. Epub 2003 Sep. 16.
50. Creput C, Durrbach A, Samuel D, Eschwege P, Amor M, Kriaa F, et al. Incidence of renal and liver rejection and patient survival rate following combined liver and kidney transplantation. American journal of transplantation: official journal of the American Society of Transplantation and the American Society of Transplant Surgeons. 2003; 3(3):348-56. Epub 2003 Mar. 5.
51. Creput C, Le Friec G, Bahri R, Amiot L, Charpentier B, Carosella E, et al. Detection of HLA-G in serum and graft biopsy associated with fewer acute rejections following combined liver-kidney transplantation: possible implications for monitoring patients. Human immunology. 2003; 64(11):1033-8. Epub 2003 Nov. 7.
52. Agaugue S, Carosella E D, Rouas-Freiss N. Role of HLA-G in tumor escape through expansion of myeloid-derived suppressor cells and cytokinic balance in favor of Th2 versus Th1/Th17. Blood. 2011; 117(26):7021-31. Epub 2011 Apr. 13.
53. Francois M, Romieu-Mourez R, Li M, Galipeau J. Human MSC suppression correlates with cytokine induction of indoleamine 2,3-dioxygenase and bystander M2 macrophage differentiation. Molecular therapy: the journal of the American Society of Gene Therapy. 2012; 20(1):187-95. Epub 2011 Sep. 22.
54. Ren G, Su J, Zhang L, Zhao X, Ling W, L'Huillie A, et al. Species variation in the mechanisms of mesenchymal stem cell-mediated immunosuppression. Stem cells. 2009; 27(8):1954-62. Epub 2009 Jun. 23.
55. Hass R, Kasper C, Bohm S, Jacobs R. Different populations and sources of human mesenchymal stem cells (MSC): A comparison of adult and neonatal tissue-derived MSC. Cell communication and signaling: CCS. 2011; 9:12. Epub 2011 May 17.
56. Sheng H, Wang Y, Jin Y, Zhang Q, Zhang Y, Wang L, et al. A critical role of IFNgamma in priming MSC-mediated suppression of T cell proliferation through up-regulation of B7-H1. Cell research. 2008; 18(8):846-57. Epub 2008 Jul. 9.
57. Kronsteiner B, Wolbank S, Peterbauer A, Hackl C, Redl H, van Griensven M, et al. Human mesenchymal stem cells from adipose tissue and amnion influence T-cells depending on stimulation method and presence of other immune cells. Stem cells and development. 2011; 20(12): 2115-26. Epub 2011 Mar. 9.
58. Ryan J M, Barry F, Murphy J M, Mahon B P. Interferon-gamma does not break, but promotes the immunosuppressive capacity of adult human mesenchymal stem cells. Clinical and experimental immunology. 2007; 149(2): 353-63. Epub 2007 May 25.
59. Xu H, Zhang G X, Ciric B, Rostami A. IDO: a double-edged sword for T(H)1/T(H)2 regulation. Immunology letters. 2008; 121(1):1-6. Epub 2008 Oct. 1.
60. Grohmann U, Fallarino F, Puccetti P. Tolerance, DCs and tryptophan: much ado about IDO. Trends in immunology. 2003; 24(5):242-8. Epub 2003 May 10.
61. Mellor A L, Munn D H. IDO expression by dendritic cells: tolerance and tryptophan catabolism. Nature reviews Immunology. 2004; 4(10):762-74. Epub 2004 Oct. 2.
62. Chen W, Liang X, Peterson A J, Munn D H, Blazar B R. The indoleamine 2,3-dioxygenase pathway is essential for human plasmacytoid dendritic cell-induced adaptive T regulatory cell generation. Journal of immunology. 2008; 181(8):5396-404. Epub 2008 Oct. 4.
63. Baratelli F, Lin Y, Zhu L, Yang S C, Heuze-Vourc'h N, Zeng G, et al. Prostaglandin E2 induces FOXP3 gene expression and T regulatory cell function in human CD4+T cells. Journal of immunology. 2005; 175(3):1483-90. Epub 2005 Jul. 22.
64. Krause P, Bruckner M, Uermosi C, Singer E, Groettrup M, Legler D F. Prostaglandin E(2) enhances T-cell proliferation by inducing the costimulatory molecules OX40L, CD70, and 4-1BBL on dendritic cells. Blood. 2009; 113(11):2451-60. Epub 2008 Nov. 26.
65. Jonuleit H, Kuhn U, Muller G, Steinbrink K, Paragnik L, Schmitt E, et al. Proinflammatory cytokines and prostaglandins induce maturation of potent immunostimulatory dendritic cells under fetal calf serum-free conditions. European journal of immunology. 1997; 27(12):3135-42. Epub 1998 Feb. 17.

66. Gavin M A; Clarke S R, Negrou E, Gallegos A, Rudensky A. Homeostasis and anergy of CD4(+)CD25(+) suppressor T cells in vivo. Nature immunology. 2002; 3(1): 33-41. Epub 2001 Dec. 12.
67. Bach J F. Regulatory T cells under scrutiny. Nature reviews Immunology. 2003; 3(3):189-98. Epub 2003 Mar. 27.
68. Gribben J G, Freeman G J, Boussiotis V A, Rennert P, Jellis C L, Greenfield E, et al. CTLA4 mediates antigen-specific apoptosis of human T cells. Proceedings of the National Academy of Sciences of the United States of America. 1995; 92(3):811-5. Epub 1995 Jan. 31.
69. Meisel R, Zibert A, Laryea M, Gobel U, Daubener W, Dilloo D. Human bone marrow stromal cells inhibit allogeneic T-cell responses by indoleamine 2,3-dioxygenase-mediated tryptophan degradation. Blood. 2004; 103(12):4619-21. Epub 2004 Mar. 6.
70. Aust L, Devlin B, Foster S J, Halvorsen Y D, Hicok K, et al. (2004) Yield of human adipose-derived adult stem cells from liposuction aspirates. Cytotherapy 6: 7-14.
71. Dubois S G, Floyd E Z, Zvonic S, Kilroy G, Wu X, et al. (2008) Isolation of human adipose-derived stem cells from biopsies and liposuction specimens. Methods Mol Biol 449: 69-79.
72. Yu G, Wu X, Dietrich M A, Polk P, Scott L K, et al. (2010) Yield and characterization of subcutaneous human adipose-derived stem cells by flow cytometric and adipogenic mRNA analyzes. Cytotherapy 12: 538-546.
73. Bourin P, Bunnell B A, Casteilla L, Dominici M, Katz A J, et al. (2013) Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT). Cytotherapy 15: 641-648.
74. Gimble J M, Bunnell B A, Frazier T, Rowan B, Shah F, et al. (2013) Adipose-derived stromal/stem cells: a primer. Organogenesis 9: 3-10.
75. McIntosh K R, Frazier T, Rowan B G, Gimble J M (2013) Evolution and future prospects of adipose-derived immunomodulatory cell therapeutics. Expert Rev Clin Immunol 9: 175-184.

What is claimed is:

1. A transplantation method comprising inducing allograft tolerance and chimerism by: a) administering, intravenously, subcutaneously, or intradermally, to a host one or more doses of human stem/progenitor-like cells, wherein said human stem/progenitor-like cells are adipose-derived stem cells isolated from fresh human subcutaneous adipose lipoaspirate; b) administering, intravenously, subcutaneously or intradermally, to a host, donor cells, wherein said donor cells are allogeneic to the host, and wherein said donor cells are unprocessed bone marrow, or low density bone marrow cells, wherein said donor cells are administered up to ten (10) days after administration of said human stem/progenitor-like cells in step (a); c) transplanting tissue, allogenic to the host but autologous to the donor cells up to ten (10) days before or after administration of said human stem/progenitor cells; and d) depleting of CD4+ and CD8+ cell of the host; and e) administering a nonmyeloablative anti-neoplastic agent.

2. The method of claim 1, wherein one or more doses of stem/progenitor-like cells is $2\times10^7$ to $10\times10^7$ cells/kg per dose.

3. The method of claim 1, wherein said donor cells are derived from cells selected from the group consisting of cord blood, committed progenitor cells, differentiated cells, vertebral body bone marrow cells, marrow cells isolated from ribs, iliac crest cells, long bone derived marrow cells, umbilical cord blood, or mobilized stem cells.

4. The method of claim 1, wherein said transplanting tissue is not rejected for at least 90 days.

5. The method of claim 1, wherein said method results in reducing expression of T-cell receptors Vβ 5.1, Vβ 5.2 and Vβ 11 by donor cells of step (b).

6. The method of claim 1, wherein said depleting of CD4$^+$ and CD8$^+$ cells is by administering of anti-CD4$^+$ and anti-CD8$^+$ antibody.

7. The method of claim 1, wherein said adipose-derived stem cells are CD45$^-$, CD73$^+$, CD90$^+$ and CD105$^+$.

8. The method of claim 1, wherein said anti-neoplastic agent is a non-specific alkylating anti-neoplastic agent.

9. The method of claim 8, wherein said alkylating anti-neoplastic agent is busulfan.

10. The method of claim 9, wherein said busulfan is administered at 5 mg/kg to 1 mg/kg.

* * * * *